United States Patent [19]

Franckowiak et al.

[11] Patent Number: 4,532,248
[45] Date of Patent: Jul. 30, 1985

[54] METHOD OF COMBATTING CORONARY AND VASCULAR DISEASES

[75] Inventors: Gerhard Franckowiak, Wuppertal; Horst Böshagen, Haan; Friedrich Bossert, Wuppertal; Siegfried Goldmann, Wuppertal; Horst Meyer, Wuppertal; Egbert Wehinger, Wuppertal; Jürgen Stoltefuss, Haan; Matthias Schramm, Cologne; Günter Thomas, Wuppertal, all of Fed. Rep. of Germany; Robertson Towart, Slough, Great Britain

[73] Assignee: Bayer Aktiengesellschaft, Leverkusen, Fed. Rep. of Germany

[21] Appl. No.: 398,034

[22] Filed: Jul. 14, 1982

[30] Foreign Application Priority Data

Jul. 30, 1981 [DE] Fed. Rep. of Germany ....... 3130041
Feb. 25, 1982 [DE] Fed. Rep. of Germany ....... 3206671

[51] Int. Cl.$^3$ ............................................. A61K 31/44
[52] U.S. Cl. ..................... 514/302; 546/116; 546/286; 546/310; 546/312; 514/63; 514/89; 514/211; 514/212; 514/218; 514/222; 514/227; 514/234; 514/236; 514/237; 514/238; 514/240; 514/241; 514/248; 514/277; 514/290; 514/296; 514/297; 514/306; 514/314; 514/320; 514/334; 514/344; 514/345; 514/352; 514/357; 514/358
[58] Field of Search ............... 424/256, 266, 200, 184, 424/263, 257, 258, 244, 248.53, 248.54; 546/286, 310, 312, 116

[56] References Cited

U.S. PATENT DOCUMENTS 3,932,645  1/1976  Meyer et al. ......................... 424/263
4,145,432  3/1979  Sato ..................................... 546/116
4,248,873  2/1981  Bossert et al. ...................... 424/256

FOREIGN PATENT DOCUMENTS 2013190  8/1979  United Kingdom .

OTHER PUBLICATIONS

Schramm et al., Nature, vol. 303, pp. 535–537, (1983).

Primary Examiner—Henry R. Jiles
Assistant Examiner—Bernard I. Dentz
Attorney, Agent, or Firm—Sprung Horn Kramer & Woods

[57] ABSTRACT 1,4-Dihydropyridines of the formula

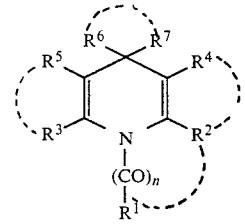

in which
n is 0,1 or 2, and
$R^1$ to $R^7$ can have a wide variety of meanings, which possess inotropic action, and many of which are new, are useful in increasing the influx of $Ca^{++}$ into cells, particularly in combatting coronary and vascular diseases, hypertension swelling in the mucous membranes and diseases involving increased blood sugar or an incorrect salt and fluid balance.

13 Claims, No Drawings

METHOD OF COMBATTING CORONARY AND VASCULAR DISEASES

The present invention relates to the use as agents with a positive inotropic action of certain dihydropyridines, some of which are known.

The invention also relates to those dihydropyridines which are novel and to a process for their production.

It has already been disclosed that 1,4-dihydropyridines possess vasodilative properties and can be used as coronary agents and antihypertensive agents (see British Pat. No. 1,173,062; British Pat. No. 1,358,951; DE-OS (German Published Specification) No. 2,629,892 and DE-OS (German Published Specification) No. 2,752,820). Furthermore, it is known that 1,4-dihydropyridines, as calcium antagonists, cause an inhibition of the contractility of smooth and cardiac muscles, and can be employed for the treatment of coronary diseases and vascular diseases (see A. Fleckenstein, Ann. Rev. Pharmacol. Toxicol. 17, 149–166 (1977)).

With a knowledge of these properties of the dihydropyridines, it could not be foreseen that the compounds according to the invention, from this substance class, would possess a positive inotropic action on the myocardium, which action augments contractility instead of inhibiting contraction.

According to the present invention we provide a pharmaceutical composition containing as an active ingredient a compound which is a 1,4-dihydropyridine of the general formula

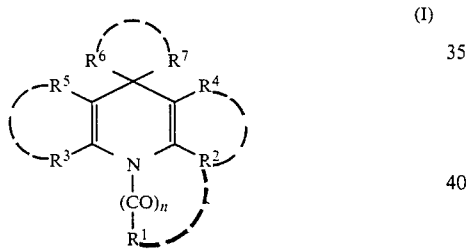

(I)

in the form of an individual isomer, an isomer mixture, a racemate or an optical antipode, or a pharmaceutically acceptable salt thereof, in which n is 0, 1 or 2, $R^1$
- (a) represents a hydrogen atom, a straight-chain, branched, cyclic, saturated or unsaturated aliphatic hydrocarbon radical which optionally contains 1 to 3 identical or different hetero chain members selected from O, CO, $SO_m$ (in which m is 0, 1 or 2), =N—, $NR^I$ and $SiR^{II}R^{III}$, this hydrocarbon radical being optionally substituted by halogen, $NO_2$, CN, $N_3$, hydroxyl, aryl or heteroaryl, or
- (b) represents an aryl or heteroaryl radical, these radicals optionally carrying 1 to 5 identical or different substituents selected from aryl, alkyl, alkenyl, alkinyl, alkenoxy, alkinoxy, aralkyl, acyl, alkylene, dioxyalkylene, halogen, $CF_3$, $OCF_3$, $SCF_3$, $NO_2$, NO, CN, $N_3$, $COR^{IV}$, $COOR^V$, $OR^{VI}$, $NR^I$ and $NR^{VII} R^{VIII}$, and it being possible for the alkyl, alkoxy and aryl radicals of the abovementioned substituents in turn to be substituted by halogen, $COR^V$ or $NR^{VII}R^{VIII}$, or
- (c) represents a radical of the general formula $NR^{VII}R^I$, (and the radicals $R^I$, $R^{II}$, $R^{III}$, $R^{IV}$, $R^V$, $R^{VI}$, $R^{VII}$ and $R^{VIII}$ mentioned under (a), (b) and (c) above having the meanings given below), $R^2$
- (a), independently of $R^1$, has any of those meanings given for $R^1$, or
- (b) represents a radical of the general formula $NHR^I$ or

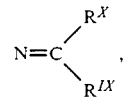

($R^I$, $R^{IX}$ and $R^X$ having the meanings given below), or $R^1$ and $R^2$ together form a 5-membered to 8-membered, saturated or unsaturated ring which optionally contains 1, 2 or 3 identical or different ring members selected from O, S, $NR^I$ and CO, and which optionally contains 1 to 3 identical or different substituents selected from halogen, hydroxyl, alkyl, alkoxy, aryl and aralkyl, $R^3$, independently of $R^2$, has any of those meanings given for $R^2$ with the proviso that only one of the substituents $R^2$ or $R^3$ can represent alkoxy, alkylthio or $NHR^I$ in each instance, $R^4$ and $R^5$, are identical or different and each
- (a) represents a halogen atom, $NO_2$, NO, CN, $SO_m$—$R^{XI}$ (in which m is 0, 1 or 2), a halogen atom,

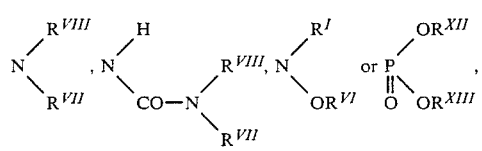

($R^I$, $R^{VII}$, $R^{VIII}$, $R^{XI}$ and $R^{XIII}$ having the meanings given below), or
- (b) represents a branched or unbranched, cyclic, saturated or unsaturated aliphatic hydrocarbon radical which is optionally substituted by halogen, OH, CN, alkoxy, alkylthio, aryloxy, $COOR^V$ or

($R^V$, $R^{VII}$ and $R^{VIII}$ having the meanings given below), or
- (c) represents an aromatic hydrocarbon radical, or a 5-membered to 7-membered saturated or unsaturated hetero ring having 1 to 4 identical or different hetero members selected from O, S, —N= and $NR^I$ ($R^I$ having the meaning given below), this hetero ring being linked to the dihydropyridine ring either via a carbon atom or a nitrogen atom, and the aromatic hydrocarbon radical and the hetero rings optionally carrying 1 to 3 identical or different substituents selected from halogen, OH, CN, $CF_3$, $OCF_3$, $SCF_3$, $NO_2$, alkyl, alkoxy, aryl and

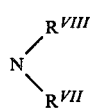

($R^{VII}$ and $R^{VIII}$ having the meanings given below), (d) represents a radical of the general formula

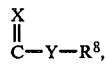

wherein X denotes oxygen, sulphur or $NR^I$, Y represents a single bond, O, S or $NR^I$ ($R^I$ having the meaning given below), and $R^8$, independently of $R^1$, has any of those meanings given for $R^1$, or (e) represents a radical of the general formula

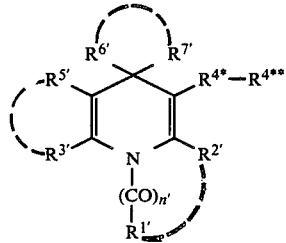

wherein n', $R^{1'}$, $R^{2'}$, $R^{3'}$, $R^{5'}$, $R^{6'}$ and $R^{7'}$, independently of n, $R^1$, $R^2$, $R^3$, $R^5$, $R^6$ and $R^7$, have any of those meanings respectively given for n, $R^1$, $R^2$, $R^3$, $R^5$, $R^6$ and $R^7$, and $R^{4*}$ and $R^{4**}$ are identical or different and each represents a radical, minus a hydrogen, of the substituents given for $R^4$ under (a) to (d), or each pair of $R^2$ and $R^4$, and/or $R^3$ and $R^5$ independently, together forms a branched, unbranched, saturated or unsaturated 5-membered to 8-membered ring which optionally contains 1, 2 or 3 identical or different ring members selected from O, CO, CS, C=$NR^I$, =N—, $NR^I$, $SO_m$ (in which m is 0, 1 or 2) and $SiR^{II}R^{III}$, and which is optionally substituted by halogen, hydroxyl, alkoxy, aryl, aralkyl,

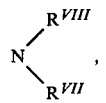

or is disubstituted by a straight-chain or branched alkylene chain having 3 to 8 carbon atoms, and the common ring of $R^2$ and $R^4$ can also be directly fused with the common ring of $R^1$ and $R^2$, (the radicals $R^I$, $R^{II}$, $R^{III}$, $R^{VII}$ and $R^{VIII}$ having the meanings given below), $R^6$ represents a hydrogen atom or an alkyl or halogenoalkyl radical, and $R^7$ (a) represents a saturated, unsaturated, cyclic, straight-chain or branched aliphatic hydrocarbon radical which is optionally substituted by halogen, aryl or heteroaryl, or (b) represents an aryl or heteroaryl radical which optionally contains 1 to 5 identical or different substituents selected from $NO_2$, CN, $N_3$, NO, $CF_3$, halogen, $COR^{IV}$, $COOR^V$, $OR^{VI}$,

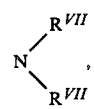

$SO_mR^{XI}$ (in which m is 0, 1 or 2),

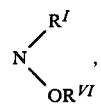

alkyl, aryl, alkenyl, alkinyl, alkenoxy, alkinoxy, aralkyl, acyl, alkylene and dioxyalkylene, and the abovementioned alkyl and aryl substituents can in turn be substituted by halogen, $COOR^V$ or

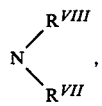

and, in the abovementioned definitions of the substituents $R^1$ to $R^8$:

$R^I$ represents a hydrogen atom or an alkyl, aryl, aralkyl, heteroaryl or acyl radical, $R^{II}$ and $R^{III}$ are identical or different and each represents an alkyl, aryl, aralkyl or heteroaryl radical, $R^{IV}$, $R^V$ and $R^{VI}$ are identical or different and each represents a hydrogen atom or an alkyl, aryl, aralkyl or heteroaryl radical (the alkyl and aryl radicals being preferably optionally substituted by halogen, nitro, trifluoromethyl, $C_1$ to $C_6$ alkylthio or $C_1$ to $C_6$ alkoxy, or additionally (in the case of aryl radicals) $C_1$ to $C_6$ alkyl), $R^{VII}$ and $R^{VIII}$ are each identical or different and represents a hydrogen atom, an aryl or aralkyl radical, or alkyl radical which is optionally interrupted by O, S or $NR^I$ ($R^I$ having the abovementioned meaning), or $R^{VII}$ and $R^{VIII}$, together with the nitrogen atom, form a 5-membered to 7-membered ring which can contain 1 or 2 identical or different hetero ring members selected from O, S or $NR^I$ ($R^I$ having the abovementioned meaning), or one of the radicals $R^{VII}$ or $R^{VIII}$ represents an aliphatic acyl group having up to 6 carbon atoms, $R^{IX}$, $R^X$, $R^{XI}$, $R^{XII}$ and $R^{XIII}$ are each identical or different and represent an alkyl, aryl or aralkyl radical, and the alkyl, aryl, aralkyl, heteroaryl and acyl radicals mentioned under $R^1$ to $R^8$ and under $R^I$ to $R^{XIII}$, and the hetero ring formed with $R^{VII}$ and $R^{VIII}$, are in turn optionally substituted by substituent(s) selected from OH, $CF_3$, $OCF_3$, CN, $NO_2$, halogen, $C_1$ to $C_6$ thioalkyl, $C_1$ to $C_6$ alkoxy, aryl and aralkyl, and additionally, except in the case of alkyl, also from alkyl, (and the following substituents may be mentioned as examples of the said heteroaryl radicals: thienyl, furyl, pyrryl, pyridyl, quinolyl, isoquinolyl, pyrimidyl, pyridazinyl, quinazolyl, quinoxalyl, benzothienyl, pyrazolyl, imidazolyl, oxazolyl, isoxazolyl, thiazolyl, triazolyl, oxdiazolyl, pyrazinyl, oxazinyl, thiazinyl, indolizinyl, indolyl, benzofuranyl, indazolyl, benzothienyl, benzimidazolyl, benzoxazolyl, benzisoxazolyl, benzthiazolyl, benztriazolyl, benzoxadiazolyl, cinnolinyl, phthalazinyl, naphthyridinyl or benzotriazinyl),
and which has positive inotropic action (as herein defined), in admixture with a solid or liquid gaseous diluent, or in admixture with a liquid diluent other than a solvent of a molecular weight less than 200 except in the presence of a surface active agent.

The pharmaceutical compositions according to the present invention which have a positive inotropic action are suitable, in particular, as cardiotonics. This contractility-augmenting effect is also based on the fact that the compounds according to the invention increase the influx of $Ca^{++}$ into the cell, and are thus also suitable for the treatment of hypotonic circulatory conditions, for the depression of blood sugar, for decreasing the swelling of mucous membranes and for influencing the salt and fluid balance.

Only compounds having positive inotropic action are included in compositions of the present invention. As used in the present application a compound is said to have "positive inotropic action" if it causes an augmentation of contraction by at least 25%, from a concentration of $10^{-5}$ g/ml, in the following test on the isolated left atrium of the guineapig heart.

Compounds may be shown to exhibit a positive inotropic action from a concentration of $10^{-5}$ g/ml, in the left atrium of the isolated guineapig heart in the following test:

Test for positive inotropic action

The left atria of guineapig hearts are isolated and suspended in a thermostated organ bath which contains an isotonic mineral salt solution adapted to the ionic environment and the pH value of body fluids, and suitable nutrients. A gas mixture consisting of oxygen and carbon dioxide is introduced into this organ bath, the carbon dioxide content being so proportioned that the pH value of the organ bath remains constant. The left atria are clamped in the organ bath, and the tension is registered by means of a force transducer, a particular fundamental tonus being established. The left atria are then continuously stimulated electrically at particular intervals, and the resulting contractions are registered. After the addition of the active compound, the contractions are further registered. As indicated, an augmentation of contraction by at least 25% is considered a significant positive-inotropic action.

The compounds used according to the present invention, of the general formula (I), can be prepared in various ways by customary methods. Their synthesis is effected, for example (A) by direct synthesis of that of the hydropyridine structure by known dihydropyridine syntheses, or (B) by modifying functional groups on the dihydropyridine skeleton according to known reaction schemes.

Further details of such processes for the production of compounds of formula (I) are given later in the description for the production of those compounds of formula (I) which are novel.

Preferred compounds for use in the compositions of the present invention are those in which
n has the abovementioned meaning,
$R^1$
(a) represents a hydrogen atom, a straight-chain, branched, cyclic, saturated or unsaturated aliphatic hydrocarbon radical which has up to 10 carbon atoms and optionally contains 1 to 2 identical or different hetero chain members selected from O, CO, S, $SO_2$, =N— or $NR^I$, this hydrocarbon radical being optionally substituted by halogen, $NO_2$, CN, $N_3$, hydroxyl, phenyl, naphthyl or heteroaryl, or (b) represents a phenyl, naphthyl or heteroaryl radical, these radicals optionally carrying 1 to 3 identical or different substituents selected from phenyl; alkyl, alkenyl, alkinyl, alkenoxy and alkinoxy, each having up to 4 carbon atoms; aralkyl having 7 to 14 carbon atoms; acyl having up to 6 carbon atoms; alkylene; dioxyalkylene having up to 4 carbon atoms in the alkylene chain; halogen; $CF_3$; $OCF_3$; $SCF_3$; $NO_2$; CN; $N_3$; $COR^{IV}$; $COOR^V$, $OR^{VI}$; $NR^I$ and $NR^{VII}R^{VIII}$; and it being possible for the alkyl, alkoxy and aryl radicals of the abovementioned substituents to be substituted in turn by halogen, $COOR^V$ or $NR^{VII}R^{VIII}$, or (c) represents a radical of the general formula $NR^{VII}R^I$, (the radicals $R^I$, $R^{II}$, $R^{III}$, $R^{IV}$, $R^V$, $R^{VI}$, $R^{VII}$, and $R^{VIII}$ mentioned under (a), (b) and (c) immediately above having the meanings given below),
$R^2$
(a), independently of $R^1$, has any of those meanings given immediately above for $R^1$, or (b) represents a radical of the general formula $NHR^I$ or

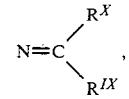

($R^I$, $R^{IX}$ and $R^X$ having the meanings given below), or $R^1$ and $R^2$ together form a 5-membered to 7-membered saturated or unsaturated ring which optionally contains one or two identical or different ring members selected from O, S, $NR^I$ and CO, and which optionally contains one to three identical or different substituents selected from halogen; hydroxyl; alkyl and alkoxy, each having 1 to 4 carbon atoms; phenyl; naphthyl; and aralkyl having 7 to 14 carbon atoms, $R^3$, independently of $R^2$, has any of those meanings given immediately above for $R^2$, with the proviso that only one of the substituents $R^2$ or $R^3$ can represent alkoxy, alkylthio or $NHR^I$ in each instance, $R^4$ and $R^5$ are identical or different and each
(a) represents a hydrogen atom, $NO_2$, NO, CN, $SO_m$—$R^{XI}$ (in which m is 0 or 2), a halogen atom,

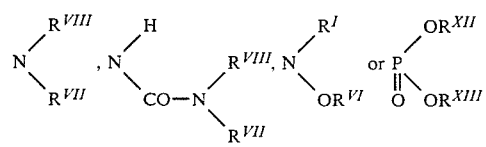

(wherein $R^I$, $R^{VII}$, $R^{VIII}$, $R^{XI}$ and $R^{XIII}$ having the meanings given below), or (b) represents a branched or unbranched cyclic, saturated or unsaturated aliphatic hydrocarbon radical which has up to 10 carbon atoms and is optionally substituted by halogen, OH, CN, alkoxy and alkylthio each having 1 to 4 carbon atoms, phenyloxy, naphthoxy, $COOR^V$ or

(wherein $R^V$, $R^{VII}$ and $R^{VIII}$ have the meanings given below), or (c) represents an aromatic hydrocarbon radical having 6 to 10 carbon atoms, or a 5-membered to 7-membered saturated or unsaturated hetero ring having 1 to 3 identical or different hetero members selected from O, S, —N=, $NR^I$ ($R^I$ having the meaning given below), and this hetero ring is linked to the dihydropyridine ring either via a carbon atom or a nitrogen atom, and the aromatic hydrocarbon radical and hetero rings optionally carry 1 to 3 identical or different substituents selected from halogen; OH; CN; $CF_3$; $OCF_3$; $SCF_3$; $NO_2$; alkyl and alkoxy, each having 1 to 4 carbon atoms; phenyl; naphthyl; and

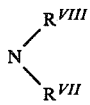

($R^{VII}$ and $R^{VIII}$ having the meanings given below), (d) represents a radical of the general formula $$\overset{X}{\underset{\|}{C}}-Y-R^8,$$

wherein X denotes oxygen, sulphur or $NR^I$, and Y represents a single bond, O, S or $NR^I$ ($R^I$ having the meaning given below), and $R^8$ independently of $R^1$ has any of those meanings given immediately above for $R^1$, or (e) represents a radical of the general formula

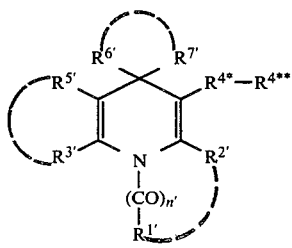

wherein n', $R^{1'}$, $R^{2'}$, $R^{3'}$, $R^{5'}$, $R^{6'}$ and $R^{7'}$, independently of n, $R^1$, $R^2$, $R^3$, $R^5$, $R^6$, and $R^7$, have any of those meanings respectively given immediately above for n, $R^1$, $R^2$, $R^3$, $R^5$, $R^6$ and $R^7$, and $R^{4*}$ and $R^{4**}$ are identical or different, and each represents a radical, minus a hydrogen, of the substituents given immediately above for $R^4$ under (a) to (d), of each pair of, $R^2$ and $R^4$, and/or $R^3$ and $R^5$, independently together forms a branched, straight-chain, saturated or unsaturated 5-membered to 7-membered ring which optionally contains 1, 2 or 3 identical or different ring members selected from O, CO, CS, $C=NR^I$, =N—, $NR^I$ and $SO_m$ (in which m is 0 or 2), and which is optionally substituted by halogen, hydroxyl, alkoxy having 1 to 4 carbon atoms, phenyl, naphthyl, aralkyl having 7 to 14 carbon atoms,

or is disubstituted by a straight-chain or branched alkylene chain having 3 to 8 carbon atoms, it also being possible for this common ring of $R^2$ and $R^4$ to be directly fused with the common ring of $R^1$ and $R^2$, (the radicals $R^I$, $R^{II}$, $R^{III}$, $R^{VII}$ and $R^{VIII}$ having the meanings given below), $R^6$ represents a hydrogen atom or an alkyl or halogenoalkyl radical each having 1 to 4 carbon atoms, and $R^7$
(a) represents a saturated, unsaturated cyclic. straight-chain or branched aliphatic hydrocarbon radical which has up to 10 carbon atoms and is optionally substituted by halogen, phenyl, naphthyl or heteroaryl, or
(b) represents a phenyl, naphthyl or heteroaryl radical which optionally contains 1 to 3 identical or different substituents selected from $NO_2$; halogen; CN; $N_3$; NO; $CF_3$; $COR^{IV}$; $COOR^V$; $OR^{VI}$;

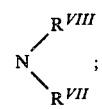

$SO_mR^{XI}$ (in which m is 0, 1 or 2);

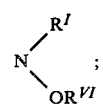

alkyl having 1 to 4 carbon atoms, phenyl; naphthyl; alkenyl, alkinyl, alkenoxy, and alkinoxy, each having up to 4 carbon atoms; aralkyl having 7 to 14 carbon atoms; acyl having 1 to 4 carbon atoms; alkylene or dioxyalkylene, each having up to 4 carbon atoms; and the abovementioned alkyl and aryl substituents in turn can be substituted by halogen, $COOR^V$ or

and, in the abovementioned definitions of the substituents $R^1$ to $R^7$:

$R^I$ represents a hydrogen atom, an alkyl radical having 1 to 6 carbon atoms, a phenyl or naphthyl radical, an aralkyl radical having 7 to 12 carbon atoms, a heteroaryl radical or an acyl radical having up to 7 carbon atoms, $R^{II}$ and $R^{III}$ are identical or different and each represents an alkyl radical having 1 to 6 carbon atoms, a phenyl radical, a naphthyl radical, an aralkyl radical having 7 to 12 carbon atoms or a heteroaryl radical, $R^{IV}$, $R^V$ and $R^{VI}$ are each identical or different and represents a hydrogen atom, an alkyl radical having 1 to 6 carbon atoms, a phenyl or naphthyl radical, an aralkyl radical having 7 to 12 carbon atoms or a heteroaryl radical (the alkyl, phenyl, naphthyl and aralkyl radicals being preferably optionally substituted by halogen; nitro; trifluoromethyl; or alkoxy, alkylthio having 1 to 4 carbon atoms or, except in the case of alkyl, also by alkyl having 1 to 4 carbon atoms), $R^{VII}$ and $R^{VIII}$ are each identical or different and represents a hydrogen atom, a phenyl or naphthyl radical, an aralkyl radical having 7 to 12 carbon atoms, or an alkyl radical which has 1 to 6 carbon atoms and which is optionally interrupted by O, S or $NR^I$, or $R^{VII}$ and $R^{VIII}$, together with the nitrogen atom, form a 5-membered to 7-membered ring which can contain 1 or 2 identical or different hetero ring members selected from O, S or $NR^I$, or one of the radicals $R^{VII}$ and $R^{VIII}$ represents an aliphatic acyl group having up to 6 carbon atoms, $R^{IX}$, $R^{XI}$, $R^{XII}$ and $R^{XIII}$ are each identical or different and represent an alkyl radical having 1 to 6 carbon atoms, a phenyl or naphthyl radical or an aralkyl radical having 7 to 12 carbon atoms, and the alkyl, aryl, aralkyl, heteroaryl and acyl radicals mentioned under $R^1$ to $R^8$ and under $R^I$ to $R^{VIII}$, and the hetero ring formed with $R^6$ and $R^7$, are in turn optionally substituted by substituent(s) selected from OH, $CF_3$, $OCF_3$, CN, $NO_2$, halogen, alkoxy having 1 to 4 carbon atoms, phenyl and benzyl, and additionally, except in the case of alkyl, also from alkyl having 1 to 4 carbon atoms, (examples of the said heteroaryl radicals being those mentioned previously in the definition of compounds of formula (I)).

Of particular interest as active compounds in the compositions of the present invention are those in which n is 0 or 1, $R^1$ (a) represents a hydrogen atom, a straight-chain, branched cyclic saturated or unsaturated aliphatic hydrocarbon radical which has up to 10 carbon atoms and which optionally contains one or two identical or different hetero chain members selected from O, CO, S, =N— or $NR^I$, this hydrocarbon radical being optionally substituted by F, Cl, Br, $NO_2$, CN, OH, phenyl or pyridyl, or (b) represents a phenyl, naphthyl or pyridyl radical, these radicals optionally carrying 1 or 2 identical or different substituents selected from phenyl; alkyl, alkenyl, alkoxy and alkenoxy, each having up to 4 carbon atoms; benzyl; acetyl; alkylene; dioxyalkylene having 2 to 4 carbon atoms; fluorine; chlorine; bromine; $CF_3$; $OCF_3$; $SCF_3$; $NO_2$; CN; $COOR^V$; $OR^{VI}$; $NR^I$ or $NR^{VII}R^{VIII}$, and it being possible for the alkyl, alkoxy and aryl radicals of the abovementioned substituents in turn to be halogen-substituted, or (c) represents a radical of the general formula $NR^{VII}R^{VIII}$, (the radicals $R^I$ to $R^{VIII}$ mentioned under (a), (b) and (c) immediately above having the meanings given below), $R^2$ (a), independently of $R^1$, has any of the meanings given immediately above for $R^1$, or (b) represents a radical of the general formula $NHR^I$ or

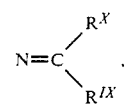

($R^I$, $R^{IX}$ and $R^X$ having the meanings given below), or $R^1$ and $R^2$ together form a 5-membered to 7-membered saturated or unsaturated ring which optionally contains 1 or 2 identical or different ring members selected from O, S, $NR^I$ or CO, and which optionally contains 1 or 2 identical or different substituents selected from halogen; hydroxyl; alkyl and alkoxy, each having 1 to 4 carbon atoms; phenyl and benzyl, $R^3$, independently of $R^2$, has any of those meanings given immediately above for $R^2$ with the proviso that only one of the substituents $R^2$ or $R^3$ can represent alkoxy, alkylthio or $NHR^I$ in each instance, $R^4$ and $R^5$ are identical or different and each (a) represents a hydrogen atom,

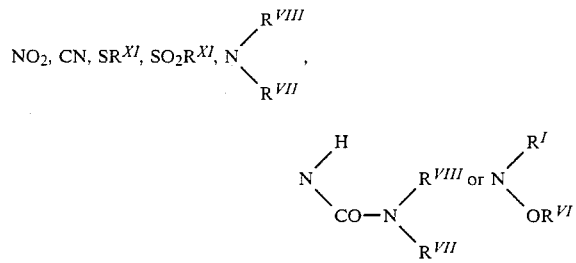

(wherein $R^I$, $R^{VI}$, $R^{VII}$, $R^{VIII}$ and $R^{IX}$ have the meanings given below), or (b) represents a branched or straight-chain alkyl or cycloalkyl radical which has up to 8 carbon atoms and which is optionally substituted by halogen, hydroxyl, cyano, alkoxy having 1 to 4 carbon atoms, phenyloxy, $COOR^V$ or

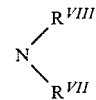

(wherein $R^V$, $R^{VII}$ and $R^{VIII}$ have the meanings given below), or (c) represents an aromatic hydrocarbon radical having 6 to 10 carbon atoms, or a 5-membered to 7-membered saturated or unsaturated hetero ring having 1 to 3 identical or different hetero members selected from O, S, =N—, $NR^I$, and this hetero ring is linked to the dihydropyridine ring either via a carbon atom or a nitrogen atom, and the aromatic hydrocarbon radical and the hetero rings optionally carry 1 or 2 identical or different substituents selected from halogen; hydroxyl; cyano; CF₃; NO₂; phenyl; and alkyl and alkoxy, each having 1 to 4 carbon atoms, or
(d) represents a radical of the general formula

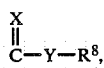

$$\overset{X}{\underset{\phantom{X}}{\|}}\!\!\!\!\!\mathrm{C}-\mathrm{Y}-\mathrm{R}^8,$$

wherein X represents oxygen or $NR^I$; and Y represents a single bond, oxygen or $NR^I$ ($R^I$ having the meaning given below), and $R^8$, independently of $R^1$, has any of those meanings given immediately above for $R^1$, or
(e) represents a radical of the general formula

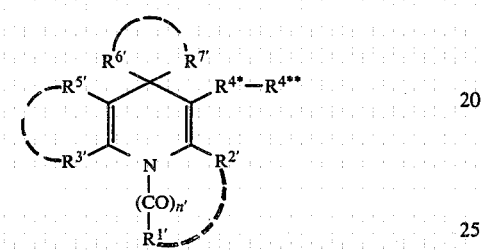

wherein n', $R^{1'}$, $R^{2'}$, $R^{3'}$, $R^{5'}$, $R^{6'}$ and $R^{7'}$, independently of n, $R^1$, $R^2$, $R^3$, $R^5$, $R^6$ and $R^7$, have any of those meanings respectively given immediately above for n, $R^1$, $R^2$, $R^3$, $R^5$, $R^6$ and $R^7$, and $R^{4*}$ and $R^{4**}$ are identical or different and each represents a radical, minus one hydrogen, of the substituents given immediately above for $R^4$ under (a) to (d), or each pair of, $R^2$ and $R^4$, and/or $R^3$ and $R^5$, independently together form a branched, straight-chain, saturated or unsaturated 5-membered to 7-membered ring which optionally contains 1 or 2 identical or different ring members selected from O, CO, CS, C=$NR^I$, =N— and $NR^I$ ($R^I$ having the meaning given below), and which is optionally substituted by halogen or hydroxyl, $R^6$ represents a hydrogen atom or an alkyl radical which has 1 to 4 carbon atoms and which is optionally substituted by fluorine, chlorine or bromine, and $R^7$
(a) represents a saturated, unsaturated cyclic, straight-chain or branched aliphatic hydrocarbon radical which has up to 8 carbon atoms and which is optionally substituted by halogen, or
(b) represents a phenyl or heteroaryl radical which optionally contains 1 to 3 identical or different substituents selected from NO₂, CN, N₃, CF₃, halogen,

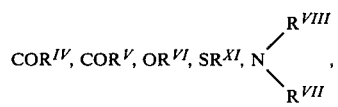

$$COR^{IV}, COR^{V}, OR^{VI}, SR^{XI}, N\!\!\begin{array}{c}\diagup R^{VIII}\\ \diagdown R^{VII}\end{array},$$

phenyl, alkyl having 1 to 4 carbon atoms, benzyl and acyl having 1 to 4 carbon atoms, and, in the abovementioned definitions of the substituents $R^1$ to $R^8$:

$R^I$ represents a hydrogen atom, an alkyl radical having 1 to 6 carbon atoms, phenyl, naphthyl, benzyl, phenethyl, heteroaryl or acyl having up to 4 carbon atoms, $R^{II}$ and $R^{III}$ are identical or different and each represents an alkyl radical having 1 to 6 carbon atoms, a phenyl radical, a naphthyl, benzyl or heteroaryl radical, $R^{IV}$, $R^V$ and $R^{VI}$ are each identical or different and represent a hydrogen atom, an alkyl radical having 1 to 6 carbon atoms, a phenyl, naphthyl, benzyl or heteroaryl radical (the alkyl, phenyl and benzyl radicals being preferably optionally substituted by fluorine, chlorine, nitro, CF₃, methoxy and methylthio and the phenyl and benzyl radicals also preferably being substituted by methyl), $R^{VII}$ and $R^{VIII}$ are each identical or different and represent a hydrogen atom, phenyl or benzyl, or alkyl which has 1 to 6 carbon atoms and which is optionally interrupted by O or $NR^I$, or $R^{VII}$ and $R^{VIII}$ together with the nitrogen atom, form a 5-membered to 7-membered ring which can contain 1 or 2 identical or different hetero ring members selected from O, S or $NR^I$, or one of the radicals $R^{VII}$ or $R^{VIII}$ represents an aliphatic acyl group having up to 6 carbon atoms, and $R^{IX}$, $R^X$, $R^{XI}$, $R^{XII}$ and $R^{XIII}$ are each identical or different and represent alkyl having 1 to 6 carbon atoms, phenyl or benzyl, (and the following substituents may be mentioned as examples of the said heteroaryl radicals: thienyl, furyl, pyrryl, pyridyl, quinolyl, isoquinolyl, pyrimidyl, pyridazinyl, quinazolyl, quinoxalyl, benzothienyl, pyrazolyl, imidazolyl, oxazolyl, isoxazolyl, thiazolyl, triazolyl, oxydiazolyl, pyrazinyl, oxazinyl, thiazinyl, indolyl, benzofuranyl, indazolyl, benzothienyl, benzimidazolyl, benzoxazolyl, benzisooxazolyl, benzthiazolyl, benztriazolyl or benzoxadiazolyl).

Of especial interest as active compounds in compositions of the present invention are those, in which n is 0, $R^1$
(a) represents a hydrogen atom, an aliphatic hydrocarbon radical which has up to 6 carbon atoms, which optionally contains a hetero chain member selected from O, CO, =N— and $NR^I$, and which is optionally substituted by halogen, nitro, hydroxyl or phenyl, or
(b) represents a phenyl or pyridyl radical which is optionally substituted by halogen, NO₂, CF₃, OCF₃, CN, $COOR^V$ or $NR^{VII}R^{VIII}$ (in which $R^V$, $R^{VII}$ and $R^{VIII}$ have the meanings which follow), $R^2$, independently of $R^1$, has any of the meanings given immediately above for $R^1$, or represents a radical of the general formula $NHR^I$ or $N=CR^XR^{XI}$ (in which $R^I$, $R^X$ and $R^{XI}$ have the meanings which follow), $R^3$, independently of $R^2$, has any of the meanings given immediately above for $R^2$, $R^4$ and $R^5$ are identical or different and each
(a) represents a hydrogen atom, NO₂, $NR^{VII}R^{VIII}$, NH—CO—$NR^{VII}R^{VIII}$ or a halogen atom, or
(b) represents an alkyl radical which has 1 to 4 carbon atoms and which is optionally substituted by halogen, OH, CN, alkoxy having 1 to 4 carbon atoms, $COOR^V$ or $NR^{VII}R^{VIII}$, or
(c) represents a phenyl, pyridyl or thienyl radical which is optionally substituted by halogen, OH, CN, alkyl or alkoxy, each having 1 to 4 carbon atoms, or by NR$^{VII}$R$^{VIII}$, (R$^V$, R$^{VII}$ and R$^{VIII}$ in (a), (b) and (c) immediately above having the meanings which follow), or (d) represents a radical of the general formula

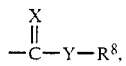

wherein X denotes oxygen and Y represents a single bond, oxygen or NR$^I$ (R$^I$ having the meaning which follows), and R$^8$ independently of R$^1$, has any of the meanings given for R$^1$ or (e) represents a radical of the general formula

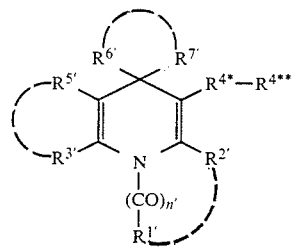

wherein n', R$^{1'}$, R$^{2'}$, R$^{3'}$, R$^{5'}$, R$^{6'}$ and R$^{7'}$, independently of n, R$^1$, R$^2$, R$^3$, R$^5$, R$^6$ and R$^7$, have any of the meanings given immediately above for n, R$^1$, R$^2$, R$^3$, R$^5$, R$^6$ and R$^7$, and R$^{4*}$ and R$^{4**}$ are identical or different and each represent a radical minus a hydrogen, of the substituents given immediately above for R$^4$ under (a) to (d), or R$^2$ and R$^4$ together form a 5-membered to 7-membered ring which optionally contains 1 or 2 different ring members selected from O, CO, CS or C=NR$^I$ and which is optionally substituted by halogen, R$^6$ represents a hydrogen atom or an alkyl having 1 to 4 carbon atoms, and R$^7$, R$^I$, R$^V$, R$^{VII}$, R$^{VIII}$, R$^X$ and R$^{XI}$ have the meanings given above in the definition of active compounds of particular interest.

Active compounds in which at least one of the substituents R$^4$ and R$^5$ represents NO$_2$, and/or in which R$^2$ and R$^4$ together, or R$^3$ and R$^5$ together, form a lactone ring may be most particularly singled out.

The preparation of the active compounds used according to the invention is effected according to customary methods which are known for the preparation of 1,4-dihydropyridines (see, for example, British Pat. No. 1,305,793; British Pat. No. 1,358,951; DE-OS (German Published Specification) No. 2,752,820; DE-OS (German Published Specification ) No. 2,847,237; DE-OS (German Published Specification) No. 2,629,892 and DE-OS (German Published Specification) No. 2,658,804).

Some of the compounds which can be used according to the invention are already known from the state of the art.

The compounds of Examples 1 to 10, 19 to 23, 26, 28, 29, 30, 31, 32, 35 to 38, 41, 42, 43, 45 and 46 to 254 are new and form a further subject of the present invention. Some of these new compounds are embraced by the general substituent definitions of the state of the art, without hitherto, however, having been specifically mentioned by name.

The present invention further provides, as new compounds, compounds of formula (I), in the form of individual isomers, isomer mixtures, racemates or optical antipodes, or pharmaceutically acceptable salts thereof, in which (i) at least one of the substituents R$^4$ and R$^5$ represents a group of the general formula

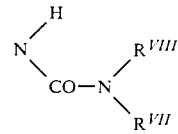

wherein
R$^{VIII}$ and R$^{VII}$ and the substituents R$^1$, R$^2$, R$^3$, R$^6$ and R$^7$ and n have the meanings given above, (ii) at least one of the substituents R$^4$ and R$^5$ represents a methyl radical and R$^1$, R$^2$, R$^3$, R$^6$ and R$^7$ and n have the meanings given above;

(iii) one of the radicals R$^4$ or R$^5$ denotes a hydrogen atom, R$^1$ represents a hydrogen atom and n is 0, and R$^2$, R$^3$, R$^6$ and R$^7$, and the other radical R$^4$ or R$^5$, have the meanings given above, and (iv) one of the radicals R$^4$ or R$^5$ denotes halogen, especially fluorine or chlorine, and R$^1$, R$^2$, R$^3$, R$^6$, R$^7$ and n and the other radical R$^4$ or R$^5$, have the meanings given above.

As indicated previously, compounds of the general formula (I) in which R$^2$ differs from R$^3$ or R$^4$ from R$^5$ can be obtained as racemic mixtures or in the form of optical isomers, owing to the presence of an asymmetric carbon atom in the 4-position of the dihydropyridine ring. Some of the compounds according to the invention which contain at least 2 asymmetric carbon atoms can be obtained in the form of individual diastereomers, or in the form of mixtures thereof.

According to the present invention we further provide a process for the production of the novel compounds of formula (I) according to the present invention, in which (a) a carbonyl compound of the general formula

in which
R$^6$ and R$^7$ have the meanings given above, is reacted with ketones of the general formulae

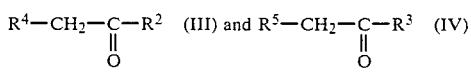

in which
R$^2$, R$^3$, R$^4$ and R$^5$ have the meanings given above, and a primary amine of the general formula $$H_2NR^1 \qquad (V)$$

in which
R$^1$ has the meaning given above, if appropriate in the presence of an inert solvent, or (b) a carbonyl compound of the general formula

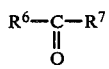 (II)

in which
R$^6$ and R$^7$ have the meanings given above, is reacted with an enamine of the general formula

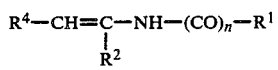 (VI)

in which
R$^1$, R$^2$, R$^4$ and n have the meanings given above and a ketone of the general formula

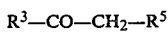 (IV)

in which
R$^3$ and R$^5$ have the meanings given above, if appropriate in the presence of an inert solvent, or
(c) an enamine of the general formula

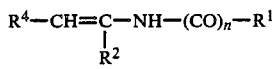 (VI)

in which
R$^1$, R$^2$, R$^4$ and n have the meanings given above, is reacted with an ylidene compound of the general formula

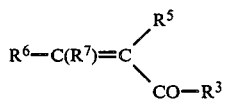 (VII)

in which
R$^3$, R$^5$, R$^6$ and R$^7$ have the meanings given above, if appropriate in the presence of an inert solvent, or
(d) modifying one or more functional groups of a dihydropyridine or a compound obtained by reaction variant (a), (b) or (c), by acid-catalyzed or base-catalyzed hydrolysis, esterification, trans-esterification, lactonization, condensation, acylation, reduction or cyclization with a reactant for such a modification, or by reaction of the intramolecular type, and separating out the individual isomers or optical antipodes, if desired, and if desired, converting the compound of formula (I) obtained by reaction variant (a), (b), (c) or (d), into a pharmaceutically acceptable salt thereof.

Reaction variants (a) to (c) correspond to the previously mentioned direct synthesis reaction (A) while reaction variant (d) corresponds to the previously mentioned reaction (B) for the modification of functional groups.

The diastereomeric mixtures obtained by reaction variant (a), (b), (c) or (d) can be separated using conventional methods. For example by fractional recrystallization or by chromatographic methods. Racemic mixtures can be separated into the particular optical isomers by customary methods, for example by cleavage or by fractional recrystallization of a salt with optically active acids.

Reaction variant (d) for the preparation of compounds according to the present invention, of the general formula (I), is carried out according to customary methods (see Houben-Weyl, Methoden der Organischen Chemie (Methods of Organic Chemistry), Georg Thieme Verlag, Stuttgart 1966; Organicum, VEB Deutscher Verlag der Wissenschaften, Berlin 1969; W. Foerst, Neuere Methoden der präparativen organischen Chemie (Recent Methods of Preparative Organic Chemistry), Vol. 1–5, Verlag Chemie, Weinheim 1961; C. Ferri, Reaktionen der organischen Chemie (Reactions of Organic Chemistry), Georg Thieme Verlag, Stuttgart 1978; Fieser+Fieser, Reagents for Organic Synthesis, Vol. 1–8, J. Wiley & Sons, Inc., London 1967.

The following have been mentioned as modification reactions of reaction variant (d): acid-catalyzed or base-catalyzed hydrolysis, esterification or trans-esterification, lactonization, condensation, acylation, reduction or cyclization using suitable reactants in each case, or reactions of the intramolecular type. Lactonization may be mentioned as being particularly advantageous. For this purpose, compounds of the general formula (I), in which the substituents R$^2$ and R$^4$ or/and R$^3$ and R$^5$ contain hydroxyl and carboxyl functions which are free and/or blocked by protective groups, are cyclized under suitable base-catalyzed or acid-catalyzed reaction conditions, if appropriate with preceding complete or partial splitting off of the protective groups, to give lactones according to the invention, of the general formula (I).

Some of the possible methods of preparation are described in more detail in DE-OS (German Published Specification) No. 2,629,892.

The definition of the substituents of the general formula (I) also embraces some compounds which have no positive inotropic action. However, by means of the abovementioned test method on an isolated guineapig atrium, the skilled worker experiences no problems in recognizing the compounds according to the invention which have a positive inotropic action, and distinguishing them from any compounds having a negative inotropic action which have been included.

The table which follows shows, by way of example, the positive inotropic (or contractility-augmenting) action, with augmentation by at least 25%, of some of the compounds according to the invention. The heading "Example No." refers to the compounds of the corresponding preparative examples which follow.

TABLE

| Example No. | Active compound concentration in g/ml | Example No. | Active compound concentration in g/ml |
|---|---|---|---|
| 1 | $10^{-7}$ | 124 | $10^{-7}$ |
| 2 | $10^{-5}$ | 126 | $10^{-6}$ |
| 3 | $10^{-6}$ | 132 | $10^{-7}$ |
| 4 | $3 \times 10^{-7}$ | 144 | $10^{-7}$ |
| 5 | $10^{-5}$ | 145 | $10^{-7}$ |
| 6 | $10^{-7}$ | 146 | $10^{-6}$ |
| 7 | $10^{-7}$ | 147 | $10^{-7}$ |
| 8 | $10^{-6}$ | 148 | $10^{-7}$ |
| 9 | $10^{-7}$ | 149 | $10^{-7}$ |
| 10 | $10^{-7}$ | 152 | $10^{-7}$ |
| 11 | $10^{-5}$ | 156 | $3 \times 10^{-7}$ |
| 12 | $10^{-6}$ | 157 | $10^{-6}$ |
| 13 | $10^{-6}$ | 158 | $10^{-7}$ |
| 14 | $10^{-6}$ | 159 | $10^{-6}$ |
| 15 | $10^{-5}$ | 164 | $10^{-6}$ |
| 16 | $10^{-6}$ | 167 | $10^{-5}$ |
| 17 | $10^{-7}$ | 170 | $10^{-6}$ |
| 18 | $3 \times 10^{-6}$ | 173 | $10^{-7}$ |
| 19 | $10^{-5}$ | 174 | $10^{-6}$ |
| 20 | $3 \times 10^{-7}$ | 175 | $10^{-5}$ |
| 21 | $10^{-7}$ | 177 | $10^{-6}$ |

TABLE-continued

| Example No. | Active compound concentration in g/ml | Example No. | Active compound concentration in g/ml |
|---|---|---|---|
| 22 | $10^{-6}$ | 179 | $3 \times 10^{-7}$ |
| 23 | $3 \times 10^{-7}$ | 181 | $10^{-6}$ |
| 24 | $10^{-5}$ | 186 | $10^{-7}$ |
| 25 | $10^{-6}$ | 187 | $10^{-7}$ |
| 26 | $10^{-7}$ | 189 | $3 \times 10^{-7}$ |
| 27 | $10^{-7}$ | 190 | $10^{-6}$ |
| 29 | $10^{-7}$ | 191 | $10^{-6}$ |
| 31 | $10^{-6}$ | 193 | $10^{-7}$ |
| 32 | $10^{-7}$ | 195 | $3 \times 10^{-6}$ |
| 33 | $10^{-7}$ | 196 | $10^{-5}$ |
| 35 | $10^{-6}$ | 197 | $3 \times 10^{-6}$ |
| 36 | $10^{-6}$ | 198 | $3 \times 10^{-7}$ |
| 37 | $10^{-6}$ | 199 | $3 \times 10^{-7}$ |
| 38 | $10^{-6}$ | 200 | $10^{-7}$ |
| 40 | $10^{-6}$ | 202 | $10^{-7}$ |
| 41 | $10^{-6}$ | 203 | $10^{-6}$ |
| 42 | $10^{-5}$ | 208 | $10^{-7}$ |
| 43 | $10^{-6}$ | 210 | $3 \times 10^{-6}$ |
| 44 | $10^{-6}$ | 211 | $10^{-6}$ |
| 45 | $10^{-6}$ | 212 | $3 \times 10^{-7}$ |
| 49 | $10^{-6}$ | 214 | $3 \times 10^{-6}$ |
| 55 | $10^{-7}$ | 215 | $3 \times 10^{-7}$ |
| 56 | $10^{-6}$ | 216 | $10^{-6}$ |
| 59 | $10^{-6}$ | 217 | $10^{-5}$ |
| 60 | $3 \times 10^{-6}$ | 218 | $10^{-5}$ |
| 64 | $10^{-6}$ | 219 | $10^{-5}$ |
| 65 | $10^{-6}$ | 220 | $10^{-6}$ |
| 67 | $3 \times 10^{-7}$ | 221 | $10^{-6}$ |
| 68 | $3 \times 10^{-7}$ | 222 | $10^{-6}$ |
| 69 | $10^{-7}$ | 223 | $3 \times 10^{-6}$ |
| 72 | $10^{-7}$ | 224 | $10^{-6}$ |
| 73 | $10^{-7}$ | 225 | $10^{-6}$ |
| 77 | $10^{-6}$ | 226 | $10^{-6}$ |
| 78 | $3 \times 10^{-6}$ | 227 | $10^{-6}$ |
| 79 | $10^{-7}$ | 228 | $10^{-6}$ |
| 80 | $10^{-7}$ | 229 | $10^{-5}$ |
| 86 | $10^{-6}$ | 230 | $10^{-7}$ |
| 88 | $10^{-6}$ | 231 | $10^{-6}$ |
| 92 | $10^{-6}$ | 232 | $10^{-6}$ |
| 93 | $10^{-6}$ | 233 | $10^{-6}$ |
| 94 | $10^{-6}$ | 234 | $10^{-6}$ |
| 98 | $10^{-7}$ | 235 | $3 \times 10^{-5}$ |
| 99 | $10^{-5}$ | 236 | $10^{-6}$ |
| 101 | $10^{-6}$ | 239 | $3 \times 10^{-7}$ |
| 102 | $10^{-6}$ | 240 | $3 \times 10^{-6}$ |
| 104 | $3 \times 10^{-7}$ | 241 | $10^{-7}$ |
| 105 | $10^{-7}$ | 242 | $3 \times 10^{-7}$ |
| 108 | $10^{-5}$ | 245 | $3 \times 10^{-7}$ |
| 111 | $3 \times 10^{-6}$ | 246 | $3 \times 10^{-7}$ |
| 112 | $10^{-7}$ | 247 | $10^{-6}$ |
| 114 | $10^{-6}$ | 248 | $3 \times 10^{-7}$ |
| 117 | $10^{-6}$ | 250 | $3 \times 10^{-7}$ |
| 118 | $10^{-7}$ | 251 | $10^{-7}$ |
|  |  | 257 | $3 \times 10^{-7}$ |

The compounds according to the invention exhibit a valuable pharmacological action spectrum, which could not be foreseen. They can be used as cardiotonics for improving the heart contractility. In addition, owing to the fact that they increase the influx of $Ca^{++}$ into the cell, they can be employed as antihypotonics, for the depression of blood sugar, for decreasing the swelling of mucous membranes, and for influencing the salt and fluid balance.

As stated above, the invention also relates to the use in human and veterinary medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampules or suppositories comprising a compound of the formula.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitan esters), microcrystalline cellulose, aluminum metahydroxide, bentonite, agar-agar and tragacanth or mixtures thereof.

All the pharmaceutical compositions according to the invention can also contain coloring agents and preservatives as well as perfumes and flavoring additions (e.g. peppermint oil and eucalyptus oil) and sweetening agents (e.g. saccharin).

The pharmaceutical compositions according to the invention generally contain from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampules. Some of these forms may be made up for delayed release of the active ingredient. Some, such as capsules, include a protective envelope which renders the portions of the medicament physically discrete and coherent.

The preferred daily dose for intravenous administration of the medicaments of the invention is 0.5 l to 25 mg of active ingredient, and for oral administration is 5 to 500 mg of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally or parenterally, especially perlingually or intravenously. Preferred pharmaceutical compositions and medicaments are therefore those adapted for administration such as oral or parenteral administration. Administration in the method of the invention is preferably oral or parenteral administration.

In general it has proved advantageous to administer intravenously amounts of from 0.001 to 1 mg/kg, preferably 0.01 to 0.5 mg/kg, of body weight per day and to administer orally amounts of from 0.01 to 20 mg/kg, preferably 0.1 to 10 mg/kg, of body weight per day, to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, while in other cases the upper limit mentioned must be exceeded to achieve the desired results. Where larger amounts are administered it can be advisable to divide these into several individual administrations over the course of the day.

The following examples illustrate processes for the production of novel compounds according to the present invention and of compounds used in the compositions according to the present invention.

PREPARATIVE EXAMPLES

Example 1

Ethyl 2-methyl-4-(2-trifluoromethylphenyl)-5-oxo-1,4-dihydro-5,7-dihydrofuro[3,4-b]pyridine-3-carboxylate

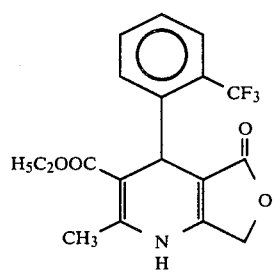

50 millimols each of ethyl 4-acetoxy-3-oxo-butyrate, ethyl 3-aminocrotonate and 2-trifluoromethylbenzaldehyde in 100 ml of ethanol were boiled under reflux for 24 hours, 2 g of potassium hydroxide were then added, and the mixture was boiled for a further hour. After the mixture had cooled, the product was precipitated with a water/sodium chloride mixture and was recrystallized from methanol.

Yield: 45% of theory; m.p.: 195° C.

Example 2

Ethyl 2-methyl-4-(3-methoxyphenyl)-5-oxo-1,4-dihydro-5,7-dihydrofuro[3,4-b]pyridine-3-carboxylate

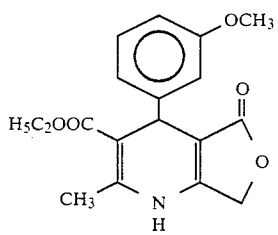

Preparation analogous to Example 1, using 3-methoxybenzaldehyde instead of 2-trifluoromethylbenzaldehyde.

Yield: 30% of theory; m.p.: 180° C.

Example 3

Ethyl 2-methyl-4-(3-chlorophenyl)-5-oxo-1,4-dihydro-5,7-dihydrofuro[3,4-b]pyridine-3-carboxylate

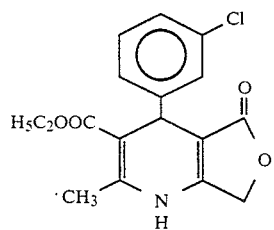

Preparation analogous to Example 1, using 3-chlorobenzaldehyde instead of 2-trifluoromethylbenzaldehyde.

Yield: 50% of theory; m.p.: 196° C.

Example 4

Propyl 2-methyl-4-(3-chlorophenyl)-5-oxo-1,4-dihydro-5,7-dihydrofuro[3,4-b]pyridine-3-carboxylate

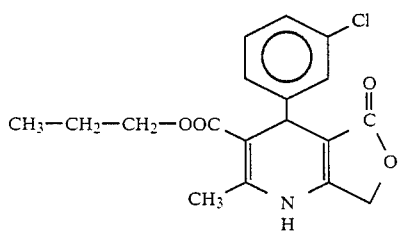

Preparation analogous to Example 1, using 3-chlorobenzaldehyde instead of 2-trifluoromethylbenzaldehyde and propyl 3-aminocrotonate instead of ethyl 3-aminocrotonate.

Yield: 42% of theory; m.p.: 166° C.

Example 5

Propyl 2-methyl-4-(3-nitrophenyl)-5-oxo-1,4-dihydropyridine-5,7-dihydrofuro[3,4-b]pyridine-3-carboxylate

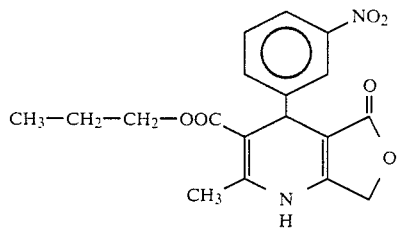

Preparation analogous to Example 1, using 3-nitrobenzaldehyde instead of 2-trifluoromethylbenzaldehyde and propyl 3-aminocrotonate instead of ethyl 3-aminocrotonate.

Yield: 50% of theory; m.p.: 196° C.

Example 6

Isopropyl 2-methyl-4-(2-trifluoromethylphenyl)-5-oxo-1,4-dihydro-5,7-dihydrofuro[3,4-b]pyridine-3-carboxylate

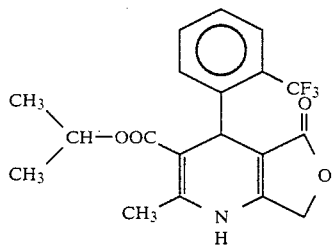

Preparation analogous to Example 1, using isopropyl 3-aminocrotonate instead of ethyl 3-aminocrotonate.

Yield 18% of theory; m.p.: 219°–223° C.

Example 7

Butyl 2-methyl-4-(2-trifluoromethylphenyl)-5-oxo-1,4-dihydro-5,7-dihydrofuro[3,4-b]pyridine-3-carboxylate

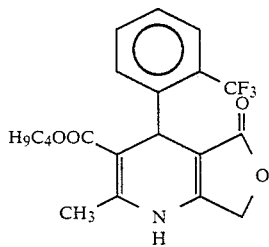

Preparation analogous to Example 1, using butyl 3-aminocrotonate instead of ethyl 3-aminocrotonate.

Yield: 10% of theory; m.p.: 194°–195° C.

Example 8

2-Methoxyethyl 2-methyl-4-(2-trifluoromethylphenyl)-5-oxo-1,4-dihydro-5,7-dihydrofuro[3,4-b]pyridine-3-carboxylate

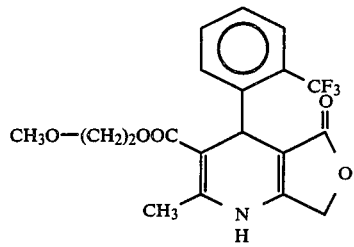

Preparation analogous to Example 1, using 2-methoxyethyl 3-aminocrotonate instead of ethyl 3-aminocrotonate.

Yield: 16% of theory; m.p.: 196°–197° C.

Example 9

Ethyl 2-methyl-4-(2-benzylthiophenyl)-5-oxo-1,4-dihydro-5,7-dihydrofuro[3,4-b]pyridine-3-carboxylate

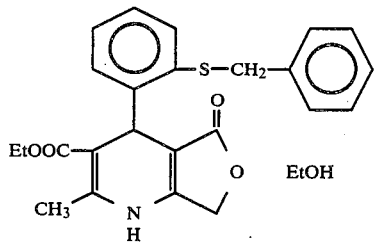

Preparation analogous to Example 1, using 2-benzylthiobenzaldehyde instead of 2-trifluoromethylbenzaldehyde.

Yield 31% of theory; m.p. 189°–190° C. (from EtOH).

Example 10

Ethyl 2-methyl-4-(2-methylphenyl)-5-oxo-1,4-dihydro-5,7-dihydrofuro[3,4-b]pyridine-3-carboxylate

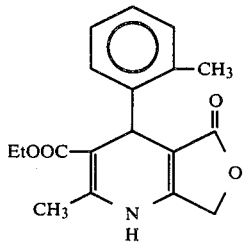

Preparation analogous to Example 1, using 2-methylbenzaldehyde instead of 2-trifluoromethylbenzaldehyde.

Yield 45%, m.p. 196°–198° C.

Example 11

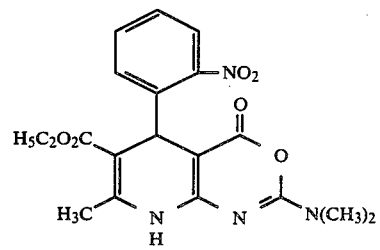

33.8 g (90 millimols) of diethyl 2-amino-1,4-dihydro-2,6-dimethyl-4-(2-nitrophenyl)-pyridine-3,5-dicarboxylate, together with 14.6 g (90 millimols) of dichloromethylene-dimethyl-ammonium chloride in 200 ml of chlorobenzene, were stirred for 2 hours at 80° C. The mixture was then cooled with ice, and the precipitated product was filtered off under suction and taken up in a cold 10% strength sodium bicarbonate solution. The aqueous phase was extracted several times with methylene chloride. After the extracts had been dried over $Na_2SO_4$ and the solvent had been distilled off, 16.6 g (46% of theory) of the reaction product of melting point m.p.: 216°–218° C. resulted.

Example 12

Methyl 1,4-dihydro-2-methyl-5-oxo-7,7-pentamethylene-4-(2'-nitrophenyl)-7H-pyrano[4,3-b]pyridine-3-carboxylate

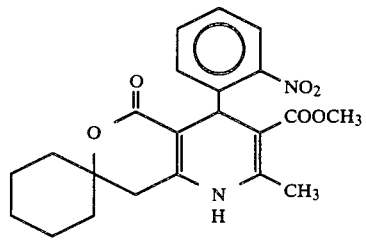

4.6 g of 6,6-pentamethylenetetrahydropyran-2,4-dione, 3.8 g of 2-nitrobenzaldehyde and 2.9 g of methyl 3-aminocrotonate in 100 ml of ethanol/glacial acetic acid (5:1) were boiled under reflux for 10 hours. The mixture was cooled to room temperature, and the precipitate was filtered off under suction. When recrystallized from ethanol, 6 g (58% of theory) of product of m.p.: 228° C. were obtained.

Example 13

Ethyl 1,4-dihydro-2,7-dimethyl-4-(2'-methylphenyl)-5-oxo-7H-pyrano[4,3-b]pyridine-3-carboxylate

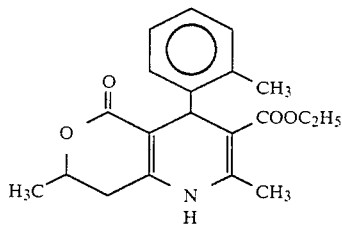

A solution of 4.3 g of 6-methyltetrahydropyran-2,4-dione, 4.0 g of 2-methylbenzaldehyde and 4.3 g of ethyl 3-aminocrotonate in 80 ml of ethanol/glacial acetic acid (5:1) was boiled under reflux for 10 hours. The mixture was concentrated in vacuo, and the residue was recrystallized from ethanol: 5.3 g (50% of theory) of m.p.: 213° C.

The following were obtained analogously:

Example 14

Ethyl 1,4-dihydro-2,7-dimethyl-4-(3'-trifuoromethylphenyl)-5-oxo-7H-pyrano[4,3-b]pyridine-3-carboxylate of m.p.: 210° C.

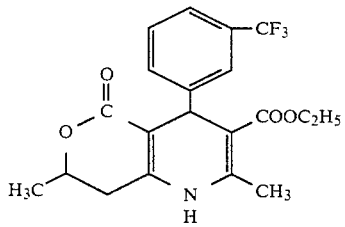

Example 15

Methyl 1,4-dihydro-2,7-dimethyl-4-(2'-chlorophenyl)-5-oxo-7H-pyrano[4,3-b]pyridine-4-carboxylate of m.p.: 252°–254° C.

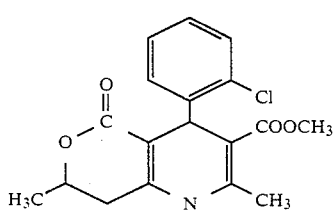

Example 16

Cyclopentyl 1,4-dihydro-2,6-dimethyl-3-nitro-4-(3-nitrophenyl)-pyridine-5-carboxylate

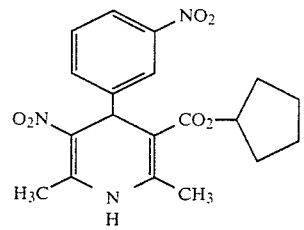

15.1 g (0.1 mol) of 3-nitrobenzaldehyde, together with 16.9 g (0.1 mol) of cyclopentyl β-aminocrotonate and 10.3 g (0.1 mol) of nitroacetone in 150 ml of ethanol, were heated under reflux for 6 hours. After the reaction mixture had cooled, the solvent was distilled off in vacuo, and the oily residue was taken up in a small amount of chloroform and was chromatographed on a silica gel column, using chloroform with the addition of methanol. The fractions containing the reaction product were concentrated, the residue was taken up in a small amount of isopropanol, and the nitrodihydropyridine crystallized in yellow crystals of melting point 174° C.

Yield: 37% of theory.

Example 17

β-n-Propoxyethyl 1,4-dihydro-2,6-dimethyl-3-nitro-4-(3-nitrophenyl)-pyridine-5-carboxylate

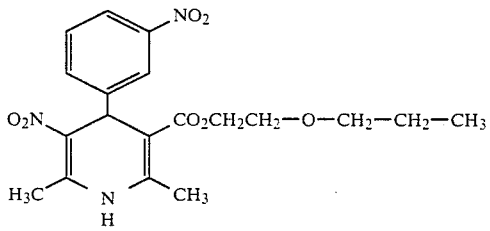

15.1 g (0.1 mol) of 3-nitrobenzaldehyde, together with 18.8 g (0.1 mol) of β-n-propoxyethyl acetoacetate and 10.2 g (0.1 mol) of 2-amino-1-nitro-prop-1-ene in 150 ml of ethanol, were heated uder reflux for 6 hours. After cooling, the solvent was distilled off in vacuo, and the oily residue was taken up in a small amount of chloroform and was chromatographed on a silica gel column, using chloroform with the addition of methanol. The fractions containing the product were concentrated, the residue was taken up in a small amount of isopropanol, and the nitrodihydropyridine crystallized in yellow crystals of melting point 161° C.

Yield: 41% of theory.

Example 18

1,4-Dihydro-2,6-dimethyl-3,5-dinitro-4-(3-nitrophenyl)-pyridine

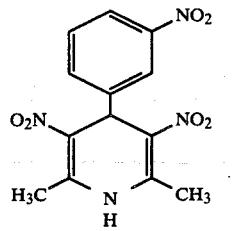

23.6 g (0.1 mol) of 2-nitro-1-(3nitrophenyl)-but-1-ene-3-one and 10.2 g (0.1 mol) of 2-amino-1-nitro-prop-1-ene in 150 ml of ethanol were heated under reflux for 12 hours. After the mixture had cooled, the solvent was distilled off in vacuo, and the oily residue was taken up in chloroform, and was chromatographed on a silica gel column, using chloroform with the addition of methanol. The product formed yellow crystals of melting point 237°–240° C. (decomposition) in isopropanol.

Yield: 38% of theory.

Example 19

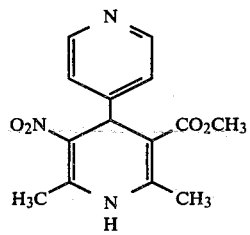

Methyl 1,4-dihydro-2,6-dimethyl-4-(pyrid-4-yl)-3-nitro-pyridine-5-carboxylate of melting point 210° C. (decomposition) (isopropanol) was obtained analogously to Example 16, by the reaction of 50 millimols of pyridine-4-aldehyde with 50 millimols of methyl acetoacetate and 50 millimols of 2-amino-1-nitro-prop-1-ene in ethanol.

Yield: 19% of theory.

EXAMPLE 20

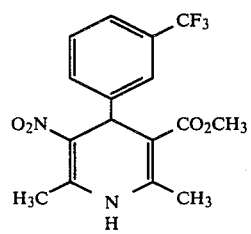

Methyl 1,4-dihydro-2,6-dimethyl-3-nitro-4-(3-trifluoromethylphenyl)-pyridine-5-carboxylate of melting point 175° C. (isopropanol) was obtained analogously to Example 16, by the reaction of 50 millimols of 3-trifluoromethylbenzaldehyde with 50 millimols of nitroacetone and 50 millimols of methyl β-aminocrotonate.

Yield: 42% of theory.

Example 21

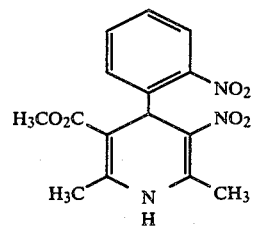

Methyl 1,4-dihydro-2,6-dimethyl-3-nitro-4-(2-nitrophenyl)-pyridine-5-carboxylate of melting point 190° C. (isopropanol) was obtained as a very photosensitive compound analogously to Example 16, by the reaction of 50 millimols of 2-nitrobenzaldehyde with 50 millimols of nitroacetone and 50 millimols of methyl β-aminocrotonate.

Yield: 12% of theory.

Example 22

β-Cyanoethyl 1,4-dihydro-2,6-dimethyl-3-nitro-4-(3-nitrophenyl)-pyridine-5-carboxylate

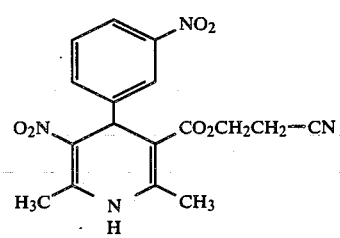

β-Cyanoethyl 1,4-dihydro-2,6-dimethyl-3-nitro-4-(3-nitrophenyl)-pyridine-5-carboxylate of melting point 210° C. (isopropanol) was obtained analgously to Example 18, by the reaction of 50 millimols of 2-nitro-1-(3-nitrophenyl)-but-1-ene-3-one with 50 millimols of β-cyanoethyl β-aminocrotonate in 100 ml of ethanol.

Yield: 33% of theory.

Example 23

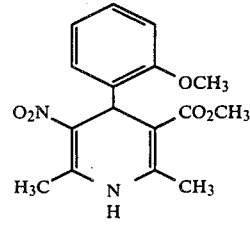

Methyl 1,4-dihydro-2,6-dimethyl-4-(2-methoxyphenyl)-3-nitro-pyridine-5-carboxylate of melting point 206° C. (ethanol) was obtained analogously to Example 18, by the reaction of 50 millimols of methyl 2-methoxybenzylideneacetoacetate and 50 millimols of 2-amino-1-nitroprop-1-ene in ethanol.

Yield: 44% of theory.

Example 24

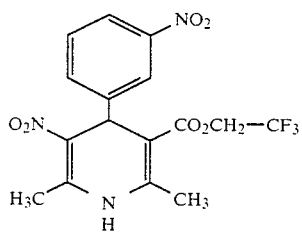

β-Trifluoroethyl 1,4-dihydro-2,6-dimethyl-3-nitro-4-(3-nitrophenyl)-pyridine-5-carboxylate of melting point 196° C. (ethanol) was obtained analogously to Example 18, by the reaction of β-trifluoroethyl 3-nitrobenzylideneacetoacetate with 2-amino-1-nitro-prop-1-ene in ethanol.

Yield: 28% of theory.

Example 25

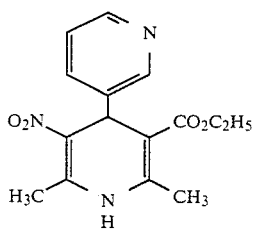

Ethyl 1,4-dihydro-2,6-dimethyl-3-nitro-4-(pyrid-3-yl)-pyridine-5-carboxylate of melting point 264° C. (isopropanol) was obtained analogously to Example 16, by the reaction of pyridine-3-aldehyde with ethyl β-aminocrotonate and nitroacetone in ethanol.

Yield: 34% of theory.

Example 26

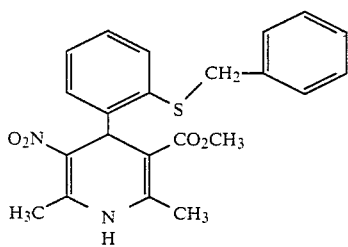

Methyl 4-(2-benzylthiophenyl)-1,4-dihydro-2,6-dimethyl-3-nitropyridine-5-carboxylate of melting point 173° C. (isopropanol) was obtained analogously to Example 17, by the reaction of 2-benzylthiobenzaldehyde with 2-amino-1-nitro-prop-1-ene and methyl acetoacetate in ethanol.

Yield: 21% of theory.

Example 27

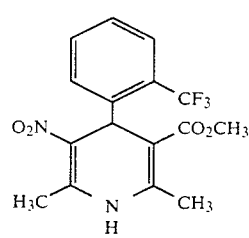

Methyl 1,4-dihydro-2,6-dimethyl-3-nitro-4-(2-trifluoromethylphenyl)-pyridine-5-carboxylate of melting point 176° C. (ethanol) was obtained analogously to Example 16, by the reaction of 2-trifluoromethylbenzaldehyde with methyl β-aminocrotonate and nitroacetone in ethanol.

Yield: 36% of theory.

Example 28

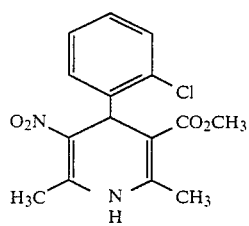

Methyl 4-(2-chlorophenyl)-1,4-dihydro-2,6-dimethyl-3-nitro-pyridine-5-carboxylate of melting point 167° C. (isopropanol) was obtained analogously to Example 16, by the reaction of 2-chlorobenzaldehyde with methyl β-aminocrotonate and nitroacetone in ethanol.

Yield: 42% of theory.

Example 29

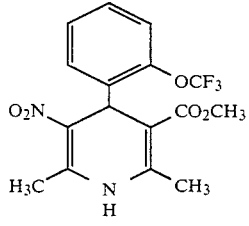

Methyl 1,4-dihydro-2,6-dimethyl-3-nitro-4-(2-trifluoromethoxyphenyl)-pyridine-5-carboxylate of melting point 175° C. (isopropanol) was obtained analogously to Example 18, by the reaction of 50 millimols of methyl 2-trifluoromethoxybenzylideneacetoacetate with 50 millimols of 2-amino-1-nitro-prop-1-ene in ethanol.

Yield: 39% of theory.

Example 30

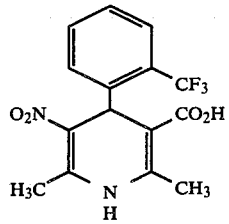

The treatment of β-cyanoethyl 1,4-dihydro-2,6-dimethyl-3-nitro-4-(2-trifluoromethylphenyl)-pyridine-5-carboxylate with 1.2 equivalents of potassium hydroxide in aqueous ethylene glycol dimethyl ether at room temperature gives, after acidification with dilute HCl, gave 1,4-dihydro-2,6-dimethyl-3-nitro-4-(2-trifluoromethylphenyl)pyridine-5-carboxylic acid of melting point 183° C. (decomposition) (methanol).

Yield 89% of theory.

Example 31

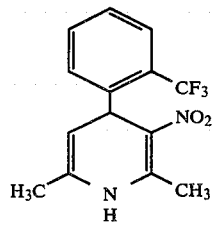

On heating in ethanol with the addition of a trace of sulphuric acid, 1,4-dihydro-2,6-dimethyl-3-nitro-4-(trifluoromethylphenyl)-pyridine-5-carboxylic acid (obtained as described in Example 30) was decarboxylated to give 1,4-dihydro-2,6-dimethyl-3-nitro-4-(trifluoromethylphenyl)pyridine in quantitative yield. Melting point 201° C.

Example 32

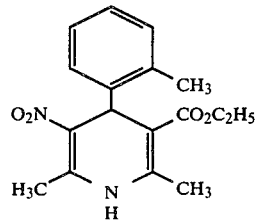

Ethyl 1,4-dihydro-2,6-dimethyl-4-(2-tolyl)-3-nitropyridine-5-carboxylate of melting point 155° C. (isopropanol) was obtained analogously to Example 18, by the reaction of ethyl 2-methyl-benzylidene-acetoacetate with 2-amino-1-nitro-prop-1-ene in ethanol.

Yield 42% of theory.

Example 33

Diethyl 2-acetylamino-4,6-dimethyl-1,4-dihydropyridine-3,5-dicarboxylate

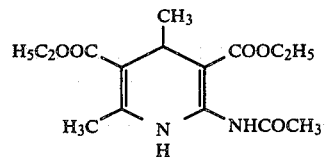

8 g (0.03 mol) of diethyl 2-amino-4,6-dimethyl-1,4-dihydropyridine-3,5-dicarboxylate in 100 ml of acetic anhydride were boiled under reflux for 4 hours. The mixture was concentrated to dryness in vacuo, and the residue was recrystallized from ethanol. Yield: 5.4 g (58% of theory) of m.p.: 105° C.

Example 34

Ethyl 2-amino-6-methyl-1,4-dihydro-4-(2'-chlorophenyl)pyridine-3-carboxylate

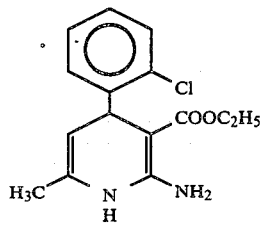

After a solution of 18.1 g of 2'-chlorobenzylidene acetone and 13.0 g of ethyl amidinoacetate in 150 ml of ethanol had been boiled for 2 hours, the solvent was stripped off in vacuo. The residue was recrystallized from ethanol, yield 62% of theory, m.p.: 171° C.

Example 35

Methyl 1,4-dihydro-4-phenyl-2,3,6-trimethylpyridine-5-carboxylate

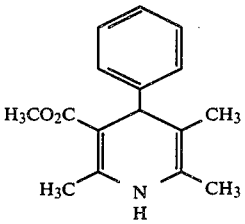

24.1 g (80 millimols) of methyl 1,4-dihydro-2,6-dimethyl-4-phenyl-pyridine-3,5-dicarboxylate were introduced in portions, at 60° C. and while stirring, into a solution of 12.2 g (320 millimols) of LiAlH$_4$ in 400 ml of absolute tetrahydrofuran (N$_2$ atmosphere), and the mixture was stirred for a further 6 to 7 hours at 60° C. After the mixture had cooled, 19.7 ml of ethyl acetate, 15.9 ml of water, 19.6 ml of 10N NaOH and 15.9 ml of water were successively added dropwise. The mixture was then filtered under suction, the residue was rinsed thoroughly with ether, and the filtrate was evaporated down in vacuo. The syrupy residue was dissolved in 50 ml of ether, and the solution was left in a cold place to crystallize giving 7.4 g of the above compound (36% of theory). After recrystallization from acetonitrile, colorless prisms; melting point 120° C., were obtained.

Example 36

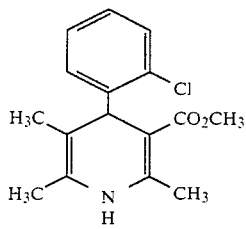

Methyl 4-(2-chlorophenyl)-1,4-dihydro-2,3,6-trimethyl-pyridine-5-carboxylate of melting point 164° C. (acetonitrile) was obtained analogously to Example 35, by reduction of methyl 4-(2-chlorophenyl)-1,4-dihydro-2,6-dimethyl-pyridine-3,5-dicarboxylate with LiAlH$_4$ in tetrahydrofuran.
Yield 30% of theory.

Example 37

Isopropyl-(2,2,2-trichloroethyl) 1,4-dihydro-2,6-dimethyl-4-(3-nitrophenyl)-pyridine-3,5-dicarboxylate

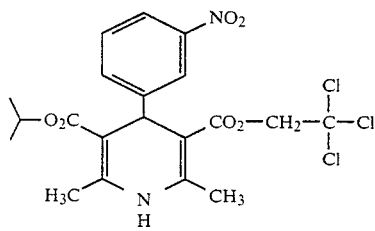

A solution of 30.2 g (0.2 mol) of 3-nitrobenzaldehyde, 46.6 g (0.2 mol) of 2,2,2-trichloroethyl acetoacetate and 28.6 g (0.2 mol) of isopropyl 3-aminocrotonate in 200 ml of ethanol was heated at the boil for 12 hours under nitrogen. The solvent was concentrated in vacuo, and the solid residue was recrystallized from ethanol. Melting point: 192° C.; yield: 46 g (47% of theory).

Example 38 n-Hexylisopropyl 1,4-dihydro-2,6-dimethyl-4-(3-nitrophenyl)-pyridine-3,5-dicarboxylate

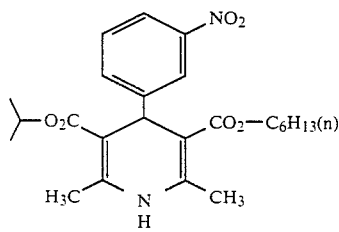

Prepared analogously to Example 32 from 0.2 mol of 3-nitrobenzaldehyde, 0.2 mol of n-hexyl acetoacetate and 0.2 mol of isopropyl 3-aminocrotonate. Melting point: 87° C.; yield: 75% of theory Example 39

Monoethyl 1,4-dihydro-2,6-dimethyl-4-(pyrid-3-yl)-pyridine-3,5-dicarboxylate

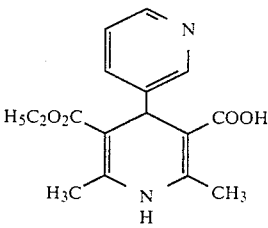

Prepared according to DE-OS (German Published Specification) 2,847,237 (Example No. 14). Melting point: 205° C. (decomposition); yield: 32% of theory.

Example 40

Methyl 3-cyano-1,4-dihydro-2,6-dimethyl-4-(2-trifluoromethylphenyl)-pyridine-5-carboxylate

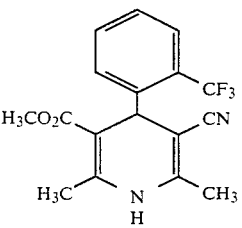

Prepared according to DE-OS (German Published Specification) 2,658,804 (Example No. 17). Melting point: 171° C.; yield: 42% of theory.

Example 41

Diethyl 2,6-di-(4-nitrophenyl)-4-(4-ethoxycarbonylmethoxy)-1-methyl-1,4-dihydropyridine-3,5-dicarboxylate

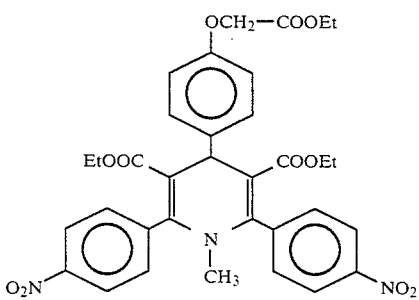

100 millimols of 4-(ethoxycarbonylmethoxy)-benzaldehyde were heated with 200 millimols of ethyl 4-nitrobenzoylacetate and 100 millimols of methylamine hydrochloride in 60 ml of pyridine at 100° C. for 5 hours. The mixture was poured onto ice-water, and the product was filtered off under suction.
Yield: 11% of theory; m.p.: 136° C.

Example 42

Diallyl 2,6-dimethyl-4-(2-trifluoromethylphenyl)-1-methyl-1,4-dihydropyridine-3,5-dicarboxylate

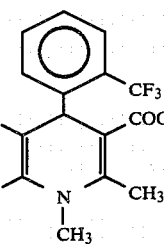

100 millimols of 2-trifluoromethylbenzaldehyde, 200 millimols of allyl acetoacetate and 120 millimols of methylamine hydrochloride in 50 ml of pyridine were heated for 5 hours at 110° C., the mixture was poured onto water, and the product was filtered off under suction.

Yield: 5% of theory; m.p.: 90° to 91° C.

Example 43

2,6-Diphenyl-3,5-di(phenylcarbonyl)-1-methyl-4-(pyrid-3-yl)-1,4-dihydropyridine

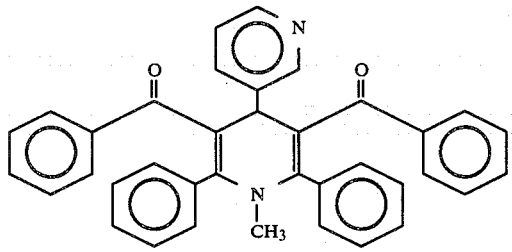

1.3 ml of pyridine-3-aldehyde, 6 g of dibenzoylmethane and 1 g of methylamine hydrochloride in 10 ml of pyridine were heated at 100° C. overnight, the mixture was then poured onto ice-water, and the product was filtered off under suction and recrystallized from methanol.

Yield: 15% of theory; m.p.: 238° C.

Example 44

Hexane-1,6-diyl bis-[2,6-dimethyl-5-ethoxycarbonyl-4-(3-nitrophenyl)-1,4-dihydropyridine-3-carboxylate]

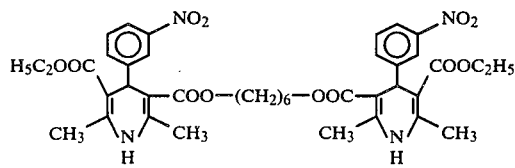

25 millimols of hexane-1,6-diyl bis-(3-aminocrotonate) together with 50 millimols of ethyl 3-nitrobenzylidene acetoacetate in 100 ml of ethanol were boiled under reflux for 14 hours. After the mixture had cooled, the solvent was distilled off in vacuo and the residue was taken up with 50% strength aqueous ethanol. The semi-solid residue was recrystallized from methanol.

Yield: 37% of theory; m.p.: 177° to 179° C.

Example 45

Dodecan-1,12-diyl bis-[2,6-dimethyl-5-ethoxycarbonyl-4-(3-nitrophenyl)-1,4-dihydropyridine-3-carboxylate]

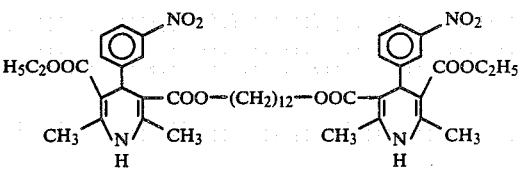

Preparation analogous to Example 44, using dodecan-1,12-diyl bis-(3-aminocrotonate) instead of hexane-1,6-diyl bis-(3-aminocrotonate).

Yield: 10% of theory; m.p.: 103° to 120° C.

Example 46

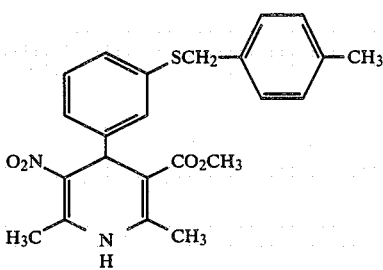

Methyl 1,4-dihydro-2,6-dimethyl-4-[2-(4-methylbenzylthio)-phenyl]-3-nitropyridine-5-carboxylate of melting point 160° C. (isopropanol) was obtained analogously to Example 17, by the reaction of 2-(4-methylbenzylthio)benzaldehyde with 2-amino-1-nitro-prop-1-ene and methyl acetoacetate in ethanol.

Yield: 28% of theory.

Example 47

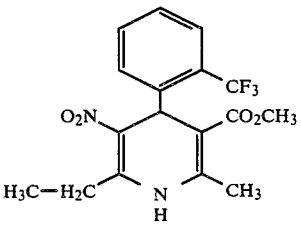

Methyl 1,4-dihydro-2-ethyl-6-methyl-3-nitro-4-(2-trifluoromethylphenyl)-pyridine-5-carboxylate of melting point 199° C. (isopropanol) was obtained analogously to Example 16, by the reaction of 2-trifluoromethylbenzaldehyde with methyl β-aminocrotonate and 1-nitrobutan-2-one in ethanol.

Yield: 31% of theory.

Example 48

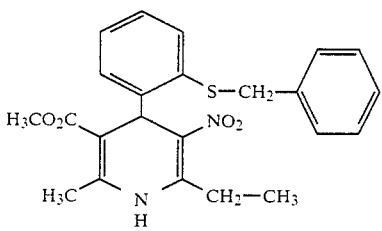

Methyl 4-(2-benzylthiophenyl)-1,4-dihydro-2-ethyl-6-methyl-3-nitro-pyridine-5-carboxylate of melting point 122° C. (isopropanol) was obtained analogously to Example 16, by the reaction of 2-benzylthiobenzaldehyde with methyl β-aminocrotonate and 1-nitrobutan-2-one in ethanol.

Yield: 21% of theory.

Example 49

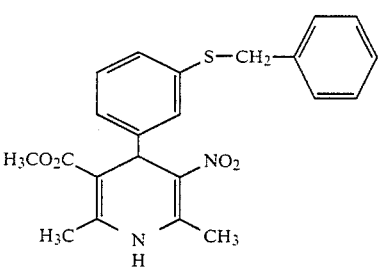

Methyl 4-(3-benzylthiophenyl)-1,4-dihydro-2,6-dimethyl-3-nitropyridine-5-carboxylate of melting point 155° C. (ethanol) was obtained analogously to Example 16, by the reaction of 3-benzylthiobenzaldehyde with methyl β-aminocrotonate and nitroacetone in ethanol.

Yield: 35% of theory.

Example 50

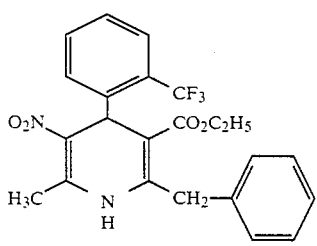

Ethyl 2-benzyl-1,4-dihydro-6-methyl-3-nitro-4-(2-trifluoromethylphenyl)-pyridine-5-carboxylate of melting point 168° C. was obtained analogously to Example 17, by the reaction of 2-trifluoromethylbenzaldehyde with ethyl γ-phenylacetoacetate and 2-amino-1-nitro-prop-1-ene in ethanol.

Yield: 12% of theory.

Example 51

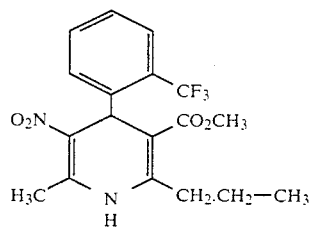

Methyl 1,4-dihydro-2-methyl-3-nitro-6-propyl-4-(2-trifluoromethyl-phenyl)-pyridine-5-carboxylate of melting point 168° C. (isopropanol) was obtained analogously to Example 17, by the reaction of 2-trifluoromethylbenzaldehyde with 2-amino-1-nitro-prop-1-ene and methyl 3-oxo-hexanoate in ethanol.

Yield: 19% of theory.

Example 52

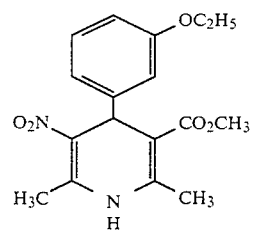

Methyl 1,4-dihydro-2,6-dimethyl-4-(3-ethoxyphenyl)-3-nitropyridine-5-carboxylate of melting point 127° C. was obtained analogously to Example 16, by the reaction of 3-ethoxybenzaldehyde with nitroacetone and methyl β-aminocrotonate in ethanol.

Yield: 42% of theory.

Example 53

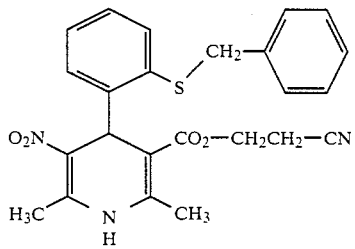

β-Cyanoethyl 4-(2-benzylthiophenyl)-1,4-dihydro-2,6-dimethyl-3-nitropyridine-5-carboxylate of melting point 173° C. (isopropanol) was obtained analogously to Example 16, by the reaction of 2-benzylthiobenzaldehyde with nitroacetone and β-cyanoethyl β-aminocrotonate in ethanol.

Yield: 28% of theory.

Example 54

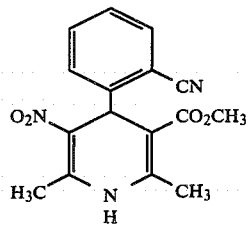

Methyl 4-(2-cyanophenyl)-1,4-dihydro-2,6-dimethyl-3-nitropyridine-5-carboxylate of melting point 182° C. (isopropanol) was obtained analogously to Example 16, by the reaction of 2-cyanobenzaldehyde with nitroacetone and methyl β-aminocrotonate in ethanol.

Yield: 28% of theory.

Example 55

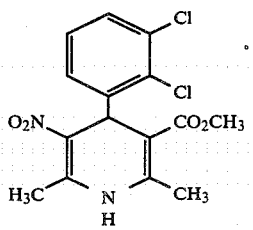

Methyl 4-(2,3-dichlorophenyl)-1,4-dihydro-2,6-dimethyl-3-nitropyridine-5-carboxylate of melting point 184° C. was obtained analogously to Example 16, by the reaction of 2,3-dichlorobenzaldehyde with nitroacetone and methyl β-aminocrotonate in ethanol.

Yield: 39% of theory.

Example 56

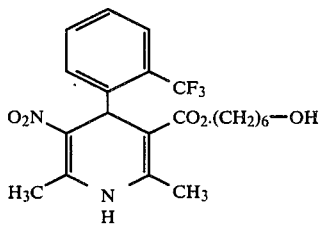

6-Hydroxyhexyl 1,4-dihydro-2,6-dimethyl-3-nitro-4-(2-trifluoromethylphenyl)-pyridine-5-carboxylate of melting point 174° C. was obtained analogously to Example 16, by the reaction of 2-trifluoromethylbenzaldehyde with nitroacetone and 6-hydroxyhexyl β-aminocrotonate in ethanol.

Yield: 32% of theory.

Example 57

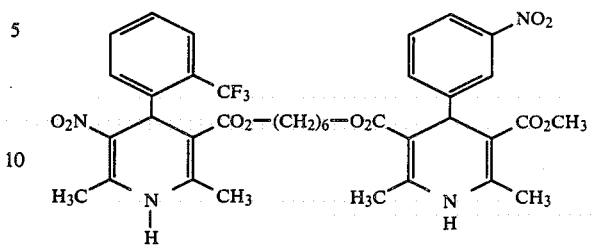

Methyl 5-(6-[2,6-dimethyl-5-nitro-4-(2-trifluoromethylphenyl)-1,4-dihydro-pyrid-3-ylcarboxy]-hexyloxycarbonyl)-2,6-dimethyl-4-(3-nitrophenyl)-1,4-dihydropyridine-3-carboxylate was obtained as an amorphous yellow substance by the reaction of 1 equivalent of 6-hydroxyhexyl 1,4-dihydro-2,6-dimethyl-3-nitro-4-(2-trifluoromethylphenyl)-pyridine-5-carboxylate with 1 equivalent of 1,4-dihydro-2,6-dimethyl-4-(3-nitrophenyl)-3-carboxymethylpyridine-5-carboxylic acid and 1.1 equivalents of dicyclohexylcarbodiimide in methylene chloride. Yield: 68% of theory. m/e: 756 M⊕

Elementary analysis

|  | C | H | N | F |
|---|---|---|---|---|
| calculated | 58.7% | 5.2% | 7.4% | 7.5% |
| found | 58.5% | 5.2% | 7.2% | 7.0% |

Example 58

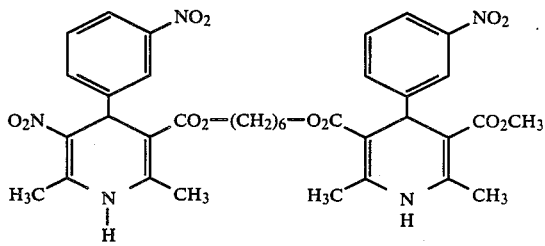

Methyl 5-(6-[2,3-dimethyl-5-nitro-4-(3-nitrophenyl)-1,4-dihydro-pyrid-3-ylcarboxy]-hexyloxycarbonyl)-2,6-dimethyl-4-(3-nitrophenyl)-1,4-dihydropyridine-3-carboxylate was obtained analogously to the previous example as an amorphous yellow substance, by the reaction of 6-hydroxyhexyl 1,4-dihydro-2,6-dimethyl-3-nitro-4-(3-nitrophenyl)-pyridine-5-carboxylate with 1,4-dihydro-2,6-dimethyl-4-(3-nitrophenyl)-3-carboxymethyl-pyridine-5-carboxylic acid and dicyclohexylcarbodiimide in methylene chloride. Yield: 73% of theory m/e: 733 M⊕

Elementary analysis

|  | C | H | N |
|---|---|---|---|
| calculated | 58.9% | 5.3% | 9.5% |
| found | 58.7% | 5.2% | 9.6% |

Example 59

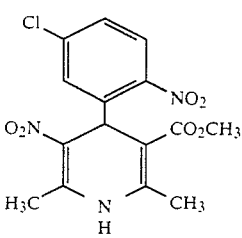

Methyl 4-(5-chloro-2-nitrophenyl)-2,4-dihydro-2,6-dimethyl-3-nitro-pyridine-5-carboxylate of melting point 221° C. (isopropanol) was obtained analogously to Example 16, by the reaction of 5-chloro-2-nitrobenzaldehyde with nitroacetone and methyl β-aminocrotonate in ethanol.
Yield: 43% of theory.

Example 60

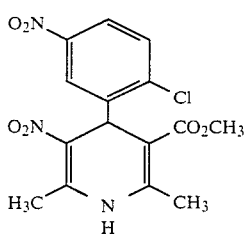

Methyl 4-(2-chloro-5-nitrophenyl)-1,4-dihydro-2,6-dimethyl-3-nitro-pyridine-5-carboxylate of melting point 219° C. was obtained analogously to Example 16, by the reaction of 2-chloro-5-nitrobenzaldehyde with nitroacetone and methyl β-aminocrotonate in ethanol.
Yield: 39% of theory.

Example 61

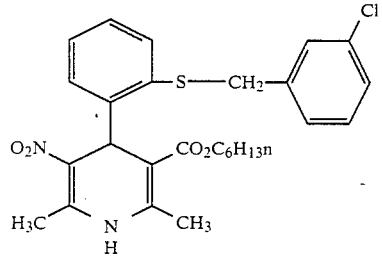

n-Hexyl 4-(3-chlorobenzylthiophenyl)-1,4-dihydro-2,6-dimethyl-3-nitropyridine-5-carboxylate was obtained analogously to Example 16, after chromatography, by the reaction of 2-(3-chlorobenzylthio)-benzaldehyde with nitroacetone and n-hexyl β-aminocrotonate in ethanol.
Yield: 21% of theory.

| Elementary analysis | C | H | Cl | N | S |
|---|---|---|---|---|---|
| calculated | 62.9% | 6.2% | 6.9% | 5.4% | 6.2% |
| found | 62.7% | 6.1% | 6.4% | 5.3% | 6.1% |

Example 62

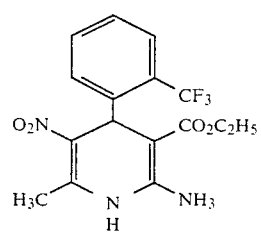

Ethyl 6-amino-1,4-dihydro-2-methyl-3-nitro-4-(2-trifluoromethylphenyl)-pyridine-5-carboxylate of melting point 210° C. (isopropanol) was obtained by the reaction of 10 millimols each of 2-trifluoromethylbenzaldehyde, nitroacetone, ethyl amidinoacetate hydrochloride and sodium methylate in 60 ml of boiling ethanol.
Yield: 36% of theory.

Example 63

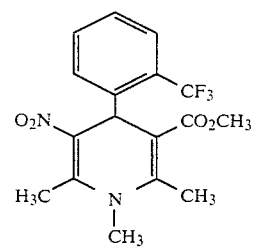

Methyl 1,4-dihydro-3-nitro-4-(2-trifluoromethylphenyl)-1,2,6-trimethylpyridine-5-carboxylate of melting point 156° C. (isopropanol) was obtained by the reaction of 10 millimols each of 2-trifluoromethylbenzaldehyde, methyl acetoacetate, nitroacetone and methylamine hydrochloride in 50 ml of glacial acetic acid at 60° C. for 12 hours.
Yield: 15% of theory.

Example 64

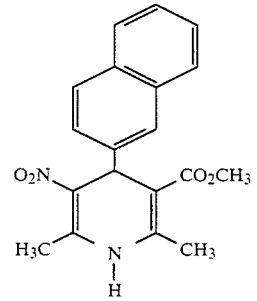

Methyl 1,4-dihydro-2,6-dimethyl-4-β-naphthyl-3-nitropyridine-5-carboxylate of melting point 163° C. (isopropanol) was obtained analogously to Example 16, by the reaction of β-naphthylaldehyde, methyl β-aminocrotonate and nitroacetone in ethanol.
Yield: 42% of theory.

Example 65

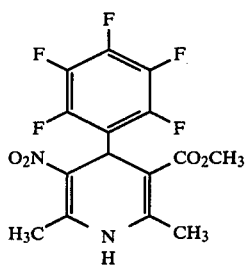

Methyl 1,4-dihydro-2,6-dimethyl-3-nitro-4-pentafluorophenylpyridine-5-carboxylate of melting point 231° C. was obtained analogously to Example 16, by the reaction of pentafluorobenzaldehyde with nitroacetone and methyl β-aminocrotonate in ethanol.

Yield: 38% of theory.

Example 66

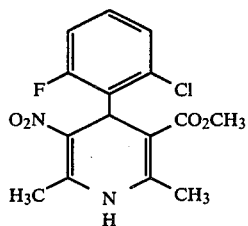

Methyl 4-(2-chloro-6-fluorophenyl)-1,4-dihydro-2,6-dimethyl-3-nitropyridine-5-carboxylate of melting point 190° C. was obtained analogously to Example 16, by the reaction of 2-chloro-6-fluorobenzaldehyde with nitroacetone and methyl β-aminocrotonate. Yield: 28% of theory.

Example 67

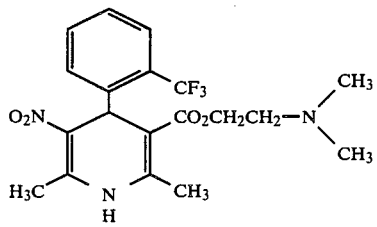

β-Dimethylaminoethyl 1,4-dihydro-2,6-dimethyl-3-nitro-4-(2-trifluoromethylphenyl)-pyridine-5-carboxylate of melting point 132° C. was obtained by the reaction of 1 equivalent each of 1,4-dihydro-2,6-dimethyl-3-nitro-4-(2-trifluoromethylphenyl)-pyridine-5-carboxylic acid with dimethylaminoethanol and dicyclohexylcarbodiimide in methylene chloride.

Yield: 84% of theory.

Example 68

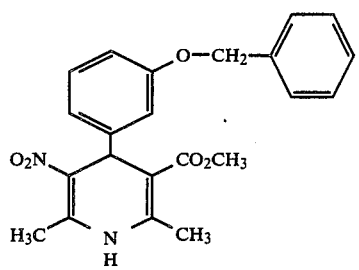

Methyl 4-(3-benzyloxyphenyl)-1,4-dihydro-2,6-dimethyl-3-nitropyridine-5-carboxylate of melting point 181° C. (isopropanol) was obtained analogously to Example 16, by the reaction of 3-benzyloxybenzaldehyde with nitroacetone and methyl β-aminocrotonate.

Yield: 34% of theory.

Example 69

Methyl 1,4-dihydro-2,6-dimethyl-4-[2-(4-methylbenzyloxy)-phenyl]-pyridine-3-carboxylate

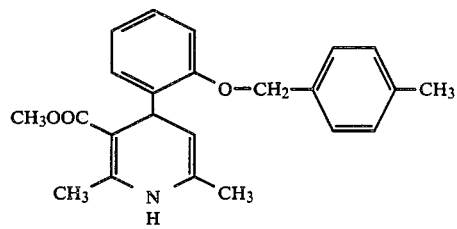

(A) Preparation of methyl α-acetyl-2-(4-methylbenzyloxy)-cinnamate 25 g (110.6 millimols) of 2-(4-methylbenzyloxy)-benzaldehyde were stirred with 11.9 ml (110.6 millimols) of methyl acetoacetate in 66 ml of isopropanol, and a freshly prepared solution of 0.64 ml of piperidine and 0.38 ml of glacial acetic acid in 5.5 ml of isopropanol was added. The mixture was stirred for 1 hour at 60° C. and for 4 hours at 40° C., and was cooled and concentrated. The residue from evaporation was dissolved in ether, and the solution was washed successively with approx. 100 ml of 1N hydrochloric acid, with two portions of water, with saturated sodium bicarbonate solution and again with two portions of water. The ether phase was dried, filtered and concentrated. 35.3 g (98.51% of theory) of a dark yellow oil were obtained, and the oil was reacted further in the crude form.

(B) Methyl-(2-cyanoethyl) 1,4-dihydro-2,6-dimethyl-4-[2-(4-methylbenzyloxy)-phenyl]-pyridine-3,5-dicarboxylate

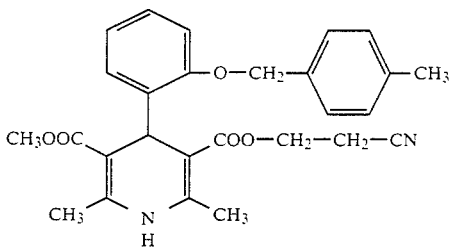

35.3 g (108.35 mollimols) of methyl α-acetyl-2-(4-methylbenzyloxy)-cinnamate and 16.8 g (108.95 millimols) of 2-cyanoethyl β-aminocrotonate in 160 ml of ethanol were boiled under reflux for 18 hours. The mixture was concentrated, the residue from evaporation was taken up in ethyl acetate, and the solution was extracted twice by shaking with water. The ethyl acetate phase was dried, filtered and concentrated. The resulting residue from evaporation crystallized when stirred with methanol. It was filtered off under suction and washed with methanol. 20.2 g (40.53% of theory) of a slightly yellow-colored product of melting point 165° C. (with decomposition) were obtained.

(C) Monomethyl 1,4-dihydro-2,6-dimethyl-4-[2-(4-methylbenzyloxy)-phenyl]-pyridine-3,5-dicarboxylate

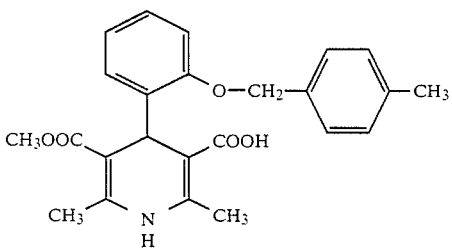

17.5 g (38 millimols) of methyl-(2-cyanoethyl) 1,4-dihydro-2,6-dimethyl-4-[2-(4-methylbenzyloxy)-phenyl]-pyridine-3,5-dicarboxylate were suspended in a solution of 4.6 g (115 millimols) of sodium hydroxide in 115 ml of water, and 57.5 ml of dimethoxyethane were added. A clear solution was gradually obtained. The solution was stirred for 20 hours, 100 ml of water were added, and the mixture was extracted three times with methylene chloride. The aqueous phase was acidified dropwise with concentrated hydrochloric acid, while stirring, and the acid was precipitated. It was filtered off under suction, washed with water and dried. 12.2 g (78.9% of theory) of a beige-colored solid product which decomposed from 169° C. were obtained.

(D)

3 g of monomethyl 1,4-dihydro-2,6-dimethyl-4-[2-(4-methylbenzyloxy)-phenyl]-pyridine-3,5-dicarboxylate were suspended in 30 ml of diethylene glycol, and the suspension was heated to 170° to 180° C. while stirring, a clear solution being formed with evolution of gas. The mixture was stirred for approx. 5 minutes at 180° C., and was cooled. The viscous solution was dissolved in an ether/water mixture with vigorous shaking, the mixture was separated, the aqueous phase was extracted with ether, and the combined ether phases were washed with 1N sodium hydroxide solution and twice with water. The ether phase was dried, filtered and concentrated. The resulting syrupy residue was crystallized in an ice-bath, using isopropanol or acetonitrile, and the crystals were filtered off under suction. 1.6 g of methyl 1,4-dihydro-2,6-dimethyl-4-[2-(4-methylbenzyloxy)-phenyl]-pyridine-3-carboxylate of melting point 107° C. to 109° C. were obtained.

The following compounds were prepared analogously:

Example 70

Ethyl 1,4-dihydro-2,6-dimethyl-4-(2-trifluoromethyl-phenyl)-pyridine-3-carboxylate of melting point 125° to 128° C.

Example 71

Isopropyl 1,4-dihydro-2,6-dimethyl-4-(3-nitro-phenyl)-pyridine-3-carboxylate, isolated as an oil. $R_f$ value: 0.525; thin layer chromatography aluminum roll, layer thickness: 0.2 mm, silica gel: 60 F 254, Merck; mobile phase: petroleum ether/ethyl acetate in the volume ratio 2:1.

Example 72

Methyl 1,4-dihydro-1,2,6-trimethyl-4-(2-chloro-phenyl)-pyridine-3-carboxylate of melting point 142° to 133° C.

Example 73

Methyl 1,4-dihydro-2,6-dimethyl-4-(3-chlorophenyl)-pyridine-3-carboxylate of melting point 129° to 133° C.

Example 74

Methyl 1,4-dihydro-2,6-dimethyl-4-(2-methyl-phenyl)-pyridine-3-carboxylate of melting point 127° to 130° C.

EXAMPLE 75

Methyl 1,4-dihydro-2,6-dimethyl-4-(2-chlorophenyl)-pyridine-3-carboxylate of melting point 143°–146° C.

Example 76

Methyl 1,4-dihydro-2,6-dimethyl-4-(3-nitrophenyl)-pyridine-3-carboxylate of melting point 110° to 112° C.

Example 77

Methyl 1,4-dihydro-2,6-dimethyl-4-(2-phenylthiomethoxy-phenyl)-pyridine-3-carboxylate as an oil.

| | | |
|---|---|---|
| Singlet | at σ = 1.6 ppm | (3H, 6-C̲H̲₃) |
| Singlet | at σ = 2.38 ppm | (3H, 2-C̲H̲₃) |
| Singlet | at σ = 3.42 ppm | (3H, COOC̲H̲₃) |
| 2 Doublets | at σ = 4.65 and 4.96 ppm | (1H each for 5H and 4H) |
| Singlet | at σ = 5.16 ppm | (1H for \N/ H ) |
| AB system | at σ = 5.5 to 5.64 ppm | (2H for —O—C̲H̲₂—S—) |

-continued

| | | |
|---|---|---|
| Multiplet | at σ = 6.9 to 7.65 ppm | (9H, aromatics) |

Example 78

Methyl 1,4-dihydro-2,6-dimethyl-4-(2-benzyloxyphenyl)-pyridine-3-carboxylate of melting point 81° to 83° C.

Example 79

Methyl 1,4-dihydro-2,6-dimethyl-4-[2-(4-chlorobenzyloxy)-phenyl]-pyridine-3-carboxylate of melting point 90° to 94° C.

Example 80

Methyl 1,4-dihydro-2,6-dimethyl-4-[2-(2-chlorobenzyloxy)-phenyl]-pyridine-3-carboxylate of melting point 75° to 77° C.

Example 81

Methyl 1,4-dihydro-2,6-dimethyl-4-[2-(2,6-dichlorobenzyloxy)-phenyl]-pyridine-3-carboxylate of melting point 125° to 128° C.

Example 82

Methyl 1,4-dihydro-2,6-dimethyl-4-[2-(3,4-dichlorophenyloxy)-phenyl]-pyridine-3-carboxylate, isolated as a foam. $R_f$ value: 0.65, prepared thin layer chromatography plates silica gel 60 F 254, mobile phase: chloroform/ethyl acetate in the volume ratio 5:1.

Example 83

Methyl 1,4-dihydro-2,6-dimethyl-4-[2-(4-methylbenzyloxy)-naphthyl]-pyridine-3-carboxylate, isolated as a foam.

Mass spectrum:

The most important peaks are found at m/e=413 (molecular peak); m/e=308; m/e=248; m/e=166.

Example 84

Isopropyl 1,4-dihydro-2,6-dimethyl-4-[2-(4-methylbenzyloxy)-phenyl]-pyridine-3-carboxylate of melting point: from 99° C.

Example 85

Methyl 1,4-dihydro-2,6-dimethyl-4-[2-(3-trifluoromethylbenzylthio)-phenyl]-pyridine-3-carboxylate, isolated as an oil. $R_f$ value: 0.84, thin layer chromatography aluminum roll, layer thickness: 0.2 mm, silica gel 60 F 254, mobile phase: chloroform/ethyl acetate in the volume ratio 5:1.

Example 86

Isobutyl 1,4-dihydro-2,6-dimethyl-4-[2-(4-methylbenzyloxy)-phenyl]-pyridine-3-carboxylate of melting point from 57° C.

Example 87

Methyl 1,4-dihydro-2,6-dimethyl-4-naphthyl-pyridine-3-carboxylate, isolated as a foam.

Mass spectrum:

The most important mass peaks are m/e=293 (molecular peak); m/e=166 (M-naphthyl).

Example 88

Methyl 1,4-dihydro-2,6-dimethyl-4-[2-(3-trifluoromethylbenzyloxy)-phenyl]-pyridine-3-carboxylate of melting point 134° C.

Example 89 sec.-Butyl 1,4-dihydro-2,6-dimethyl-4-[2-(4-methylbenzyloxy)-phenyl]-pyridine-3-carboxylate of melting point: from 78° C.

Example 90

Methyl 1,4-dihydro-2,6-dimethyl-4-(3-benzyloxyphenyl)-pyridine-3-carboxylate, isolated as an oil. $R_f$ value: 0.69, thin layer chromatography aluminum roll, layer thickness 0.2 mm, silica gel 60 G 254, Merck; mobile phase: chloroform/ethyl acetate in the volume ratio 7:1.

Example 91

Isobutyl 1,4-dihydro-2,6-dimethyl-4-[2-(3-trifluoromethylbenzyloxy)-phenyl]-pyridine-3-carboxylate, isolated as an oil.

Mass spectrum:

The most important mass peaks are: m/e=459 (molecular peak); m/e=402

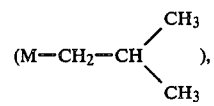

m/e=208 (M—$C_{14}H_{10}F_3O$).

Example 92

Methyl 1,4-dihydro-2,6-dimethyl-4-[2-(3-nitrobenzyloxy)-phenyl]-pyridine-3-carboxylate of melting point 117° to 118° C.

Example 93

Ethyl 1,4-dihydro-2,6-dimethyl-4-[2-(3-nitrobenzyloxy)-phenyl]-pyridine-3-carboxylate of melting point: from 107° to 109° C.

Example 94

Methyl 1,4-dihydro-2,6-dimethyl-4-[2-(4-fluorobenzyloxy)-phenyl]-pyridine-3-carboxylate of melting point 68° to 70° C.

Example 95 sec.-Butyl 1,4-dihydro-2,6-dimethyl-4-[2-(3-trifluoromethylbenzyloxy)-phenyl]-pyridine-3-carboxylate, isolated as an oil.

Mass spectrum:

The most important mass peaks are: m/e=459 (molecular peak); m/e=402 (M-57).

Example 96

Ethyl 1,4-dihydro-2,6-dimethyl-4-[2-(4-fluorobenzyloxy)-phenyl]-pyridine-3-carboxylate of melting point 122° to 125° C.

Example 97

Methyl 1,4-dihydro-2,6-dimethyl-4-[2-(3,5-dimethylbenzyloxy)-phenyl]-pyridine-3-carboxylate of melting point 127° to 129° C. (crystallizes with 1 mol of acetonitrile).

Example 98

Ethyl 1,4-dihydro-2,6-dimethyl-4-(3-nitrophenyl)-pyridine-3-carboxylate of melting point 107° to 108° C.

Example 99 n-Butyl 1,4-dihydro-2,6-dimethyl-4-[2-(3,5-dimethylbenzyloxy)-phenyl]-pyridine-3-carboxylate, isolated as an oil.

Mass spectrum:

The most important peaks are at: m/e=417 (M-2); m/e=300 (M-119) and m/e=208.

Example 100 n-Butyl 1,4-dihydro-2,6-dimethyl-4-[2-(3-methylbenzyloxy)-phenyl]-pyridine-3-carboxylate of melting point 104° to 10° C.

Example 101

Methyl 1,4-dihydro-2,6-dimethyl-4-[2-(3-methylbenzyloxy)-phenyl]-pyridine-3-carboxylate of melting point 58° to 62° C., crystallized with 1 mole of acetonitrile.

Example 102

Methyl 1,4-dihydro-2,6-dimethyl-4-[2-(3-fluorobenzyloxy)-phenyl]-pyridine-3-carboxylate of melting point 109° to 110° C.

Example 103 n-Butyl 1,4-dihydro-2,6-dimethyl-4-[2-(3-fluorobenzyloxy)-phenyl]-pyridine-3-carboxylate of melting point 105° to 106° C.

Example 104

Methyl 1,4-dihydro-2,6-dimethyl-4-(2-phenylpropylmercaptophenyl)-pyridine-3-carboxylate, isolated as an oil. R$_f$ value: 0.46, thin layer chromatography aluminum roll, layer thickness: 0.2 mm, silica gel 60 F 254 Merck, mobile phase: chloroform.

Example 105

Methyl 1,4-dihydro-2,6-dimethyl-4-[2-(3-methoxybenzyloxy)-phenyl]-pyridine-3-carboxylate of melting point: from 53° C.

Example 106

Methyl 1,4-dihydro-2,6-dimethyl-4-(2-benzylthiophenyl)-pyridine-3-carboxylate.

Mass spectrum:

The most important peaks are found at m/e=365 (molecular peak), m/e=350 (M-15), m/e=306 (M-59), m/e=274, m/e=166.

Example 107 n-Butyl 1,4-dihydro-2,6-dimethyl-4-[2-(3-methoxybenzyloxy)-phenyl]-pyridine-3-carboxylate of melting point 144° to 146° C.

Example 108

Methyl 1,4-dihydro-2,6-dimethyl-4-(2-chlorophenyl)-5-phenyl-ureidopyridine-3carboxylate

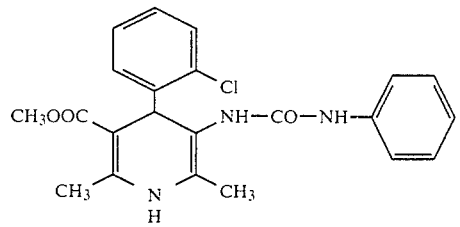

9.65 g (30 millimols) of monoethyl 1,4-dihydro-2,6-dimethyl-4-(2-chlorophenyl)-3,5-dicarboxylate were heated under reflux for 1 hour with 6.4 ml (30 millimols) of diphenylphosphorylazide and 4.2 ml (30 millimols) of triethylamine. The mixture was cooled, 2.8 ml (30 millimols) of aniline were added, and the mixture was boiled for 1 hour. The mixture was concentrated, the solid residue from evaporation was dissolved in warm ethyl acetate, and the solution was washed with 1N hydrochloric acid, water and 2N sodium hydroxide solution and twice with water, and was dried and concentrated. 100 ml of hot ethyl acetate were added to the solid residue from evaporation, the mixture was cooled while stirring, and the product was filtered off under suction and washed with ethyl acetate. 4.6 g of methyl 1,4dihydro-2,6-dimethyl-4-(2-chlorophenyl)-5-phenylureidopyridine-3-carboxylate of melting point 203° to 205° C. were obtained.

The following compounds were prepared analogously:

Example 109

Methyl 1,4-dihydro-2,6-dimethyl-4-[2-(4-methylbenzyloxy)-phenyl]-5-n-butylureido-pyridine-3-carboxylate of melting point 194° to 196° C.

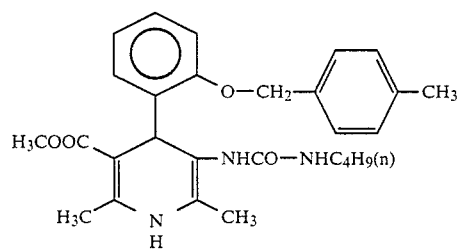

Example 110

Methyl 1,4-dihydro-2,6-dimethyl-4-(2-chlorophenyl)-5-(N-morpholinyl)-carbonylamino-pyridine-3-carboxylate of melting point 245° to 249° C.

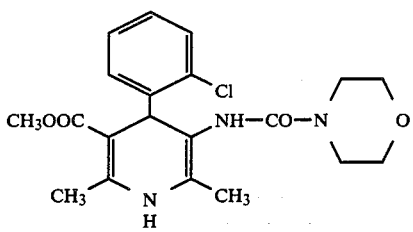

Example 111

Methyl 1,4-dihydro-2,6-dimethyl-4-(2-chlorophenyl)-5-(4-N-methylpiperazinyl-carbonylamino)-pyridine-3-carboxylate of melting point 231° C.

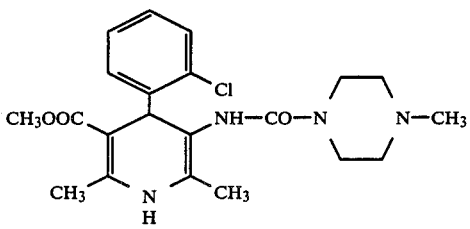

Example 112

Monomethyl 1,4-dihydro-2,6-dimethyl-4-(2-benzyloxyphenyl)-pyridine-3,5-dicarboxylate

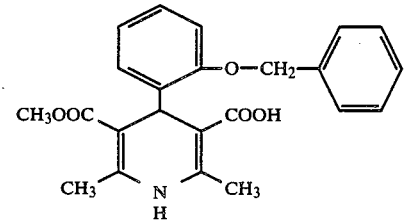

10.6 g (24 millimols) of methyl-(β-cyanoethyl) 1,4-dihydro-2,6-dimethyl-4-(2-benzyloxyphenyl)-pyridine-3,5-dicarboxylate were suspended in a solution of 2.88 g (72 millimols) of sodium hydroxide in 72 ml of water, and 45 ml of dimethoxyethane were added. The mixture was stirred overnight, 100 ml of water were added, and the mixture was extracted three times with ether. The aqueous phase was subjected to incipient distillation for a short time in a rotary evaporator, and was then acidified dropwise with concentrated hydrochloric acid, while stirring. The precipitated product was filtered off under suction, washed with water and dried. 6.2 g of a beige-colored product of melting point 160° C. (with decomposition) were obtained.

The following compounds were prepared analogously to Example 112:

Example 113

Monomethyl 1,4-dihydro-2,6-dimethyl-4-[2-(4-methylbenzyloxy)-phenyl]-pyridine-3,5-dicarboxylate of melting point 169° C. (with decomposition).

Example 114

Monomethyl 1,4-dihydro-2,6-dimethyl-4-[2-(4-chlorobenzyl)-phenyl]-pyridine-3,5-dicarboxylate of melting point 156° C. (with decomposition).

Example 115

Monomethyl 1,4-dihydro-2,6-dimethyl-4-[2-(2-chlorobenzyloxy)-phenyl]-pyridine-3,5-dicarboxylate of melting point 153° C. (with decomposition).

Example 116

Monomethyl 1,4dihydro-2,6-dimethyl-4-(2-phenylmercaptomethoxyphenyl)-pyridine-3,5-dicarboxylate of melting point 95° C. (with decomposition).

Example 117

Monomethyl 1,4-dihydro-2,6-dimethyl-4-(2-phenethyloxyphenyl)-pyridine-3,5-dicarboxylate of melting point 100° to 103° C. (with decomposition).

Example 118

Monomethyl 1,4-dihydro-2,6-dimethyl-4-[2-(2,6-dichlorobenzyloxy)-phenyl]-pyridine-3,5-dicarboxylate of melting point 198° to 201° C. (with decomposition).

Example 119

Monomethyl 1,4-dihydro-2,6-dimethyl-4-[2-(3,4-dichlorobenzyloxy)-phenyl]-pyridine-3,5-dicarboxylate of melting point 138° to 140° C. (with decomposition).

Example 120

Monomethyl 1,4-dihydro-2,6-dimethyl-4-(3-propoxyphenyl)-pyridine-3,5-dicarboxylate of melting point 175° to 177° C. (with decomposition).

Example 121

Monomethyl 1,4-dihydro-2,6-dimethyl-4-(3-benzyloxyphenyl)-pyridine-3,5-dicarboxylate of melting point 148° C. (with decomposition).

Example 122

Monomethyl 1,4-dihydro-2,6-dimethyl-4-[2-(4-methylbenzyloxy)-naphthyl]-pyridine-3,5-dicarboxylate of melting point 171° to 179° C. (with decomposition).

Example 123

Monomethyl 1,4-dihydro-2,6-dimethyl-4-naphthyl-pyridine-3,5-dicarboxylate of melting point 175° to 179° C. (with decomposition).

Example 124

Monoisopropyl 1,4-dihydro-2,6-dimethyl-4-[2-(4-methylbenzyloxy)-phenyl]-pyridine-3,5-dicarboxylate of melting point 101° C. (with decomposition).

Example 125

Monomethyl 1,4-dihydro-2,6-dimethyl-4-[2-(3-trifluoromethylbenzylthio)-phenyl]-pyridine-3,5-dicarboxylate of melting point 90° C. (with decomposition).

Example 126

Monoisobutyl 1,4-dihydro-2,6-dimethyl-4-[2-(4-methylbenzyloxy)-phenyl]-pyridine-3,5-dicarboxylate of melting point 85° C. (with decomposition).

Example 127

Mono-sec.-butyl 1,4-dihydro-2,6-dimethyl-4-[2-(4-methylbenzyloxy)-phenyl]-pyridine-3,5-dicarboxylate of melting point 133° to 140° C. (with decomposition).

Example 128

Monomethyl 1,4-dihydro-2,6-dimethyl-4-[2-(3-trifluoromethylbenzyloxy)-phenyl]-pyridine-3,5-dicarboxylate of melting point 182° C. (with decomposition).

Example 129

Monoisobutyl 1,4dihydro-2,6-dimethyl-4-[2-(3-trifluoromethylbenzyloxy)-phenyl]-pyridine-3,5-dicarboxylate of melting point 150° to 153° C. (with decomposition).

Example 130

Mono-sec.-butyl 1,4-dihydro-2,6-dimethyl-4-[2-(3-trifluoromethylbenzyloxy)-phenyl]-pyridine-3,5-dicarboxylate of melting point 144° C. (with decomposition).

Example 131

Monomethyl 1,4-dihydro-2,6-dimethyl-4-[2-(3-nitrobenzyloxy)-phenyl]-pyridine-3,5-dicarboxylate of melting point 167° C. (with decomposition).

Example 132

Monoethyl 1,4-dihydro-2,6-dimethyl-4-[2-(3-nitrobenzyloxy)-phenyl]-pyridine-3,5-dicarboxylate of melting point 172° C. (with decomposition).

Example 133

Monoethyl 1,4-dihydro-2,6-dimethyl-4-[2-(4-fluorobenzyloxy)-phenyl]-pyridine-3,5-dicarboxylate of melting point 154° to 156° C. (with decomposition).

Example 134

Monomethyl 1,4-dihydro-2,6-dimethyl-4-[2-(4-fluorobenzyloxy)-phenyl]-pyridine-3,5-dicarboxylate of melting point 181° to 186° C. (with decomposition).

Example 135

Monomethyl 1,4-dihydro-2,6-dimethyl-4-(2-(3-phenylpropyl)-mercaptophenyl)-pyridine-3,5-dicarboxylate of melting point from 94° C. (with decomposition).

Example 136

Monomethyl 1,4-dihydro-2,6-dimethyl-4-[2-(3,5-dimethylbenzyloxy)-phenyl]-pyridine-3,5-dicarboxylate of melting point from 98° C. (with decomposition).

Example 137

Mono-n-butyl 1,4-dihydro-2,6-dimethyl-4-[2-(3,5-dimethylbenzyloxy)-phenyl]-pyridine-3,5-dicarboxylate of melting point from 85° C. (with decomposition).

Example 138

Monomethyl 1,4-dihydro-2,6-dimethyl-4-[3-(4-methylbenzyloxy)-phenyl]-pyridine-3,5-dicarboxylate of melting point 140° to 145° C. (with decomposition).

Example 139

Mono-n-butyl 1,4-dihydro-2,6-dimethyl-4-[2-(3-methylbenzyloxy)-phenyl]-pyridine-3,5-dicarboxylate of melting point 132° to 139° C. (with decomposition).

Example 140

Monomethyl 1,4-dihydro-2,6-dimethyl-4-[2-(3-fluorobenzyloxy)-phenyl]-pyridine-3,5-dicarboxylate of melting point 146° to 149° C. (with decomposition).

Example 141

Mono-n-butyl 1,4-dihydro-2,6-dimethyl-4-[2-(3-fluorobenzyloxy)-phenyl]-pyridine-3,5-dicarboxylate of melting point 141° to 144° C. (with decomposition).

Example 142

Monomethyl 1,4-dihydro-2,6-dimethyl-4-[2-(3-methoxybenzyloxy)-phenyl]-pyridine-3,5-dicarboxylate of melting point 155° to 160° C. (with decomposition).

Example 143

Mono-n-butyl 1,4-dihydro-2,6-dimethyl-4-[2-(3-methoxybenzyloxy)-phenyl]-pyridine-3,5-dicarboxylate of melting point 145° to 149° C. (with decomposition).

Example 144

Ethyl 1-ethyl-2-methyl-4-[2-(3-trifluoromethylbenzylthio)-phenyl]-5-oxo-1,4,5,7-tetrahydrofuro[3,4-b]pyridine-3-carboxylate.
M.p.: 117° to 119° C.

Example 145

2-Methoxyethyl 2-methyl-4-[2-(3-trifluoromethylbenzylthio)-phenyl]-5-oxo-1,4,5,7-tetrahydrofuro[3,4-b]pyridine-3-carboxylate. M.p.: 124° to 125° C.

Example 146

Butyl 2-methyl-4-[2-(3-ttrifluoromethylbenzylthio)-phenyl]-5-oxo-1,4,5,7-tetrahydrofuro[3,4-b]pyridine-3-carboxylate. M.p.: 112° to 120° C.

Example 147

Ethyl 2-methyl-4-[2-(3-trifluoromethylbenzyloxy)-phenyl]-5-oxo-1,4,5,7-tetrahydrofuro[3,4-b]pyridine-3-carboxylate.
M.p.: 180° to 183° C.

Example 148

Ethyl 2-methyl-4-[2-(3-nitrobenzylthio)-phenyl]-5-oxo-1,4,5,7-tetrahydrofuro[3,4-b]pyridine-3-carboxylate. M.p.: 164° to 166° C.

Example 149 n-Butyl 2-methyl-4-[2-(3-nitrobenzylthio)-phenyl]-5-oxo-1,4,5,7-tetrahydrofuro[3,4-b]pyridine-3-carboxylate. M.p.: 137° to 139° C.

Example 150

Ethyl 2-methyl-4-[2-(3-methylbenzylsulphinyl)-phenyl]-5-oxo-1,4,5,7-tetrahydrofuro[3,4-b]pyridine-3-carboxylate. M.p.: 243°–245° C.

Example 151

Ethyl 4-[2-(benzylthio)-phenyl]-2-methyl-5-oxo-4,5,6,7-tetrahydro-1H-pyrrolo[3,4-b]pyridine-3-carboxylate. M.p.: 243° to 246° C.

Example 152

Ethyl 4-[2-(benzylsulphonyl)-phenyl]-2-methyl-5-oxo-1,4,5,7-tetrahydrofuro[3,4-b]pyridine-3-carboxylate. M.p.: 150° to 152° C.

Example 153

Methyl 2-methyl-4-[2-(3-trifluoromethylbenzylthio)-phenyl]-5-oxo-1,4,5,7-tetrahydrofuro[3,4-b]-3-carboxylate.
M.p.: 178° to 181° C.

Example 154

Butyl 4-[2-(4-tert.-butylbenzylthio)-phenyl]-2-methyl-5-oxo-1,4,5,7-tetrahydrofuro[3,4-b]pyridine-3-carboxylate.
M.p.: 103° C.

Example 155

Ethyl 2-methyl-4-[2-(3-trifluoromethylbenzyl)-phenyl]-5-oxo-1,4,5,7-tetrahydrofuro[3,4-b]pyridine-3-carboxylate.
M.p.: 189° C.

Example 156

Ethyl 2-methyl-4-[2-(3-methylbenzylthio)-phenyl]-5-oxo-1,4,5,7-tetrahydrofuro[3,4-b]pyridine-3-carboxylate. M.p.: 150° to 155° C.

Example 157

Butyl 4-[2-(3-chlorobenzylthio)-phenyl]-2-methyl-5-oxo-1,4,5,7-tetrahydrofuro[3,4-b]pyridine-3-carboxylate. M.p.: 167° to 170° C.

Example 158

Ethyl 4-[2-(4-ethoxycarbonylbenzylthio)-phenyl]-2-methyl-5-oxo-1,4,5,7-tetrahydrofuro[3,4-b]pyridine-3-carboxylate.
M.p.: 157° to 160° C.

Example 159

Ethyl 4-[2-benzylthio)-phenyl]-2-propyl-5-oxo-1,4,5,7-tetrahydrofuro[3,4-b]pyridine-3-carboxylate.
M.p.: 167° to 169° C.

Example 160

Ethyl 4-[2-(chlorobenzylthio)-phenyl]-2-methyl-5-oxo-1,4,5,7-tetrahydrofuro[3,4-b]pyridine-3-carboxylate. M.p.: 87° to 89° C.

Example 161

Methyl 4-[2-(benzylthio)-phenyl]-2-ethyl-5-oxo-1,4,5,7-tetrahydrofuro[3,4-b]pyridine-3-carboxylate.
M.p.: 174° to 176° C.

Example 162

Ethyl 4-[2-(4-tert.-butylbenzylthio)-phenyl]-2-methyl-5-oxo-1,4,5,7-tetrahydrofuro[3,4-b]pyridine-3-carboxylate. M.p.: 127° to 130° C.

Example 163

Ethyl 2-methyl-4-[2-(3-methylbenzylthio)-phenyl]-5-oxo-1,4,5,7-tetrahydrofuro[3,4-b]pyridine-3-carboxylate. M.p.: 114° to 116° C.

Example 164

Methyl 4-[2-(4-tert.-butylbenzylthio)-phenyl]-2-methyl-5-oxo-1,4,5,7-tetrahydrofuro[3,4-b]pyridine-3-carboxylate. M.p.: 112° to 113° C.

Example 165

Methyl 2-methyl-4-[2-(3-methylbenzylthio)-phenyl]-5-oxo-1,4,5,7-tetrahydrofuro[3,4-b]pyridine-3-carboxylate. M.p.: 166° to 168° C.

Example 166

Methyl 4-[2-(3-chlorobenzylthio)-phenyl]-2-methyl-5-oxo-1,4,5,7-tetrahydrofuro[3,4-b]pyridine-3-carboxylate. M.p.: 209° to 211° C.

Example 167

Octyl 2-methyl-4-[2-(4-methylbenzylthio)-phenyl]-5-oxo-1,4,5,7-tetrahydrofuro[3,4-b]pyridine-3-carboxylate.
$^1$H-NMR (CDCl$_3$): $\delta$=0.9 (t, J=7 Hz, 3H), 1.0–1.5 (m, 12H), 2.3 and 2.35 (2s, each 3H), 3.75–4.1 (m, 2H), 4.1 and 4.15 (2d, J=14 Hz, each 1H), 4.45 (s, 2H), 5.5 (s, 1H), 7.0–7.4 (m, 8H), 8.1 (s, NH) ppm.

Example 168

Butyl 2-methyl-4-[2-(4-methylbenzylthio)-phenyl]-5-oxo-1,4,5,7-tetrahydrofuro[3,4-b]pyridine-3-carboxylate. M.p.: 87° to 89° C.

Example 169

Ethyl 4-[2-(benzylthio)-phenyl]-2-methyl-5-oxo-1-propyl-1,4,5,7-tetrahydrofuro[3,4-b]pyridine-3-carboxylate. M.p.: 132° C.

Example 170

Ethyl 1-allyl-4-[2-(benzylthio)-phenyl]-2-methyl-5-oxo-1,4,5,7-tetrahydrofuro[3,4-b]pyridine-3-carboxylate. M.p.: 115° to 177° C.

Example 171

(2-Methoxy)-ethyl 2-methyl-4-[2-(4-methylbenzylthio)-phenyl]-5-oxo-1,4,5,7-tetrahydrofuro[3,4-b]pyridine-3-carboxylate. M.p.: 137° to 139° C.

Example 172

Ethyl 2-methyl-4-[2-(4-methylbenzyloxy)-phenyl]-5-oxo-1,4,5,7-tetrahydrofuro[3,4-b]pyridine-3-carboxylate. M.p.: 208° to 209° C.

Example 173

Ethyl 4-[2-(benzylthio)-phenyl]-1-ethyl-2-methyl-5-oxo-1,4,5,7-tetrahydrofuro[3,4-b]pyridine-3-carboxylate. M.p.: 80° to 82° C.

Example 174

Ethyl 4-[2-(benzylthio)-phenyl]-1,2-dimethyl-5-oxo-1,4,5,7-tetrahydrofuro[3,4-b]pyridine-3-carboxylate.
M.p.: 188° to 190° C.

Example 175

Ethyl 4-[3-(benzylthio)-phenyl]-2-methyl-5-oxo-1,4,5,7-tetrahydrofuro[3,4-b]pyridine-3-carboxylate.
M.p.: 183° to 185° C.

Example 176

Ethyl 4-[2-(4-methoxycarbonylbenzylthio)-phenyl]-2-methyl-5-oxo-1,4,5,7-tetrahydrofuro[3,4-b]pyridine-3-carboxylate. M.p.: 102° to 110° C.

Example 177

Ethyl 2-methyl-4-[2-(1-phenylethylthio)-phenyl]-5-oxo-1,4,5,7-tetrahydrofuro[3,4-b]pyridine-3-carboxylate. M.p.: 93° to 110° C. (2:3 diastereomer mixture).

Example 178

Ethyl 2-methyl-4-[2-(2-methylbenzylthio)-phenyl]-5-oxo-1,4,5,7-tetrahydrofuro[3,4-b]pyridine-3-carboxylate. M.p.: 217° to 219° C.

Example 179

Ethyl 2-methyl-5-oxo-4-[3-phenylpropylsulphinyl)-phenyl]-1,4,5,7-tetrahydrofuro[3,4-b]pyridine-3-carboxylate. M.p.: 185° to 186° C.

Example 180

Ethyl 2-methyl-4-[2-(4-nitrobenzylthio)-phenyl]-5-oxo-1,4,5,7-tetrahydrofuro[3,4-b]pyridine-3-carboxylate. M.p.: 168° to 170° C.

Example 181

Ethyl 4-[2-(methoxycarbonyl)-phenyl]-2-methyl-5-oxo-1,4,5,7-tetrahydrofuro[3,4-b]pyridine-3-carboxylate. M.p.: 240° to 249° C.

Example 182

Ethyl 4-[2-(butylthio)-phenyl]-2-methyl-5-oxo-1,4,5,7-tetrahydrofuro[3,4-b]pyridine-3-carboxylate. M.p.: 163° to 167° C.

Example 183

Ethyl 4-[2-(2,5-dichlorobenzylthio)-phenyl]-2-methyl-5-oxo-1,4,5,7-tetrahydrofuro[3,4-b]pyridine-3-carboxylate. M.p.: 244° to 250° C.

Example 184

Ethyl 4-[2-(4-methoxybenzylthio)-phenyl]-2-methyl-5-oxo-1,4,5,7-tetrahydrofuro[3,4-b]pyridine-3-carboxylate. M.p.: 83° to 85° C.

Example 185

Ethyl 4-[2-(4-chlorobenzylthio)-phenyl]-2-methyl-5-oxo-1,4,5,7-tetrahydrofuro[3,4-b]pyridine-3-carboxylate. M.p.: 97° to 99° C.

Example 186

Ethyl 2-methyl-4-[2-(1-methylethylthio)-phenyl]-5-oxo-1,4,5,7-tetrahydrofuro[3,4-b]pyridine-3-carboxylate. M.p.: 193° to 194° C.

Example 187

Ethyl 2-methyl-5-oxo-4-[2-(3-phenylpropylthio)-phenyl]-1,4,5,7-tetrahydro[3,4-b]pyridine-3-carboxylate. M.p.: 179° to 180° C.

Example 188

Ethyl 2-methyl-5-oxo-4-[2-(tetralin-2-yl-methylthio)-phenyl]-1,4,5,7-tetrahydrofuro[3,4-b]pyridine-3-carboxylate. M.p.: 102° to 104° C.

Example 189

Ethyl 4-(2,3-dimethylphenyl)-2-methyl-5-oxo-1,4,5,7-tetrahydrofuro[3,4-b]pyridine-3-carboxylate. M.p.: 225° to 227° C.

Example 190

Ethyl 2-methyl-5-oxo-[2-(2-[phenylcarbonyloxy]ethylthio)-phenyl]-1,4,5,7-tetrahydrofuro[3,4-b]pyridine-3-carboxylate. M.p.: 190° to 196° C.

Example 191

Ethyl 2-methyl-4-[2-(1-naphthylmethylthio)-phenyl]-5-oxo-1,4,5,7-tetrahydrofuro[3,4-b]pyridine-3-carboxylate. M.p.: 93° to 100° C.

Example 192

Ethyl 4-[2-(benzylsulphinylthio)-phenyl]-2-methyl-5-oxo-1,4,5,7-tetrahydrofuro[3,4-b]pyridine-3-carboxylate. M.p.: 250° C.

Example 193

Ethyl 4-[2-(3,4-dichlorobenzylthio)-phenyl]-2-methyl-5-oxo-1,4,5,7-tetrahydrofuro[3,4-b]pyridine-3-carboxylate. M.p.: 90° to 95° C.

Example 194

Ethyl 4-[3-benzyloxyphenyl]-2-methyl-5-oxo-1,4,5,7-tetrahydrofuro[3,4-b]pyridine-3-carboxylate. M.p.: 103° to 104° C.

Example 195

Ethyl 4-[2-(2-hydroxyethylthio)-phenyl]-2-methyl-5-oxo-1,4,5,7-tetrahydrofuro[3,4-b]pyridine-3-carboxylate. M.p.: 130° to 134° C.

Example 196

Ethyl 4-(2-benzylphenyl)-2-methyl-5-oxo-1,4,5,7-tetrahydrofuro[3,4-b]pyridine-3-carboxylate. M.p.: 239° to 240° C.

Example 197

Ethyl 4-(2-ethylthio)-phenyl-2-methyl-5-oxo-1,4,5,7-tetrahydrofuro[3,4-b]pyridine-3-carboxylate. M.p.: 235° to 236° C.

Example 198

Ethyl 2-methyl-4-[2-(methylthio)-phenyl]-5-oxo-1,4,5,7-tetrahydrofuro[3,4-b]pyridine-3-carboxylate. M.p.: 233° to 234° C.

Example 199

Ethyl 2-methyl-4-[2-(2-phenylethylthio)-phenyl]-5-oxo-1,4,5,7-tetrahydrofuro[3,4-b]pyridine-3-carboxylate. M.p.: 184° to 185° C.

Example 200

Ethyl 2-methyl-4-[2-(4-methylbenzylthio)-phenyl]-5-oxo-1,4,5,7-tetrahydrofuro[3,4-b]pyridine-3-carboxylate. M.p.: 132° to 134° C.

Example 201

Methyl 4-(2-benzyloxyphenyl)-2-methyl-5-oxo-1,4,5,7-tetrahydrofuro[3,4-b]pyridine-3-carboxylate. M.p.: 245° to 246° C.

Example 202

Ethyl 4-(2-ethylphenyl)-2-methyl-5-oxo-1,4,5,7-tetrahydrofuro[3,4-b]pyridine-3-carboxylate. M.p.: 197° to 200° C.

Example 203

Octyl 4-(2-benzylthiophenyl)-2-methyl-5-oxo-1,4,5,7-tetrahydrofuro[3,4-b]pyridine-3-carboxylate. M.p.: 212° C.

Example 204

Butyl 4-(2-benzylthiophenyl)-2-methyl-5-oxo-1,4,5,7-tetrahydrofuro[3,4-b]pyridine-3-carboxylate (amorphous substance).

Example 205

Ethyl 4-(2-benzyloxyphenyl)-2-methyl-5-oxo-1,4,5,7-tetrahydrofuro[3,4-b]pyridine-3-carboxylate. M.p.: 177° C.

Example 206

Methyl 4-(2-benzylthiophenyl)-2-methyl-5-oxo-1,4,5,7-tetrahydrofuro[3,4-b]pyridine-3-carboxylate. M.p.: 215° C.

Example 207

Ethyl 2-methyl-5-oxo-4-(2-trifluoromethylphenyl)-1,4,5,7-tetrahydrofuro[3,4-b]pyridine-3-carboxylate. M.p.: 228° to 230° C.

Example 208

Isopropyl 4-(2-benzylthiophenyl)-2-methyl-5-oxo-1,4,5,7-tetrahydrofuro[3,4-b]pyridine-3-carboxylate. M.p.: 158° to 161° C.

Example 209

Ethyl 2-methyl-5-oxo-4-(2-phenylphenyl)-1,4,5,7-tetrahydrofuro[3,4-b]pyridine-3-carboxylate. M.p.: 217° to 220° C.

Example 210

Isopropyl 2-methyl-4-(2-methylphenyl)-5-oxo-1,4,5,7-tetrahydrofuro[3,4-b]pyridine-3-carboxylate. M.p.: 208° C.

Example 211

Butyl 2-methyl-4-(2-methylphenyl)-5-oxo-1,4,5,7-tetrahydrofuro[3,4-b]pyridine-3-carboxylate. M.p.: 167° to 176° C.

Example 212

Allyl 2-methyl-4-(2-methylphenyl)-5-oxo-1,4,5,7-tetrahydrofuro[3,4-b]pyridine-3-carboxylate. M.p.: 170° to 175° C.

Example 213

3-Acetyl-4-(2-benzylthiophenyl)-2-methyl-5-oxo-1,4,5,7-tetrahydrofuro[3,4-b]pyridine. M.p.: 212° C.

Example 214

Methyl 2-methyl-5-oxo-4-(2-trifluoromethylphenyl)-1,4,5,7-tetrahydrofuro[3,4-b]pyridine-3-carboxylate. M.p.: 229° to 233° C.

Example 215

Methyl 2-methyl-5-oxo-4-(2-methylphenyl)-1,4,5,7-tetrahydrofuro[3,4-b]pyridine-3-carboxylate. M.p.: 196° to 201° C.

Example 216

2-Methoxyethyl 4-(3-chlorophenyl)-1,2-dimethyl-5-oxo-1,4,5,7-tetrahydrofuro[3,4-b]pyridine-3-carboxylate. M.p.: 128° to 133° C.

Example 217

3-Acetyl-2-methyl-5-oxo-4-[2-trifluoromethylphenyl]-tetrahydrofuro[3,4-b]pyridine. M.p.: 212° to 213° C.

Example 218

Ethyl 2-methoxymethyl-5-oxo-4-(2-trifluoromethylphenyl)-1,4,5,7-tetrahydrofuro[3,4-b]pyridine-3-carboxylate. M.p.: 218° to 219° C.

Example 219

Ethyl 4-(3-chlorophenyl)-1,2-dimethyl-5-oxo-1,4,5,7-tetrahydrofuro[3,4-b]pyridine-3-carboxylate. M.p.: 188° to 190° C.

Example 220

Butyl 4-(3-chlorophenyl)-2-methyl-5-oxo-1,4,5,7-tetrahydrofuro[3,4-b]pyridine-3-carboxylate. M.p.: 142° to 144° C.

Example 221

Allyl 4-(3-chlorophenyl)-2-methyl-5-oxo-1,4,5,7-tetrahydrofuro[3,4-b]pyridine-3-carboxylate. M.p.: 164°-167° C.

Example 222

(2-Pyridyl)-methyl 2-methyl-5-oxo-4-(2-trifluoromethylphenyl)-1,4,5,7-tetrahydrofuro[3,4-b]pyridine-3-carboxylate. M.p.: 209° to 210° C.

Example 223

Ethyl 2-methyl-5-oxo-1-propyl-4-(2-trifluoromethylphenyl)-1,4,5,7-tetrahydrofuro[3,4-b]pyridine-3-carboxylate. M.p.: 106° to 107° C.

Example 224

Benzyl 2-methyl-5-oxo-4-(2-trifluoromethylphenyl)-1,4,5,7-tetrahydrofuro[3,4-b]pyridine-3-carboxylate. M.p.: 218° to 219° C.

Example 225

Hexyl 4-(3-chlorophenyl)-2-methyl-5-oxo-1,4,5,7-tetrahydrofuro[3,4-b]pyridine-3-carboxylate. M.p.: 130° to 133° C.

Example 226

Ethyl 1-ethyl-2-methyl-5-oxo-4-(2-trifluoromethylphenyl)-1,4,5,7-tetrahydrofuro[3,4-b]pyridine-3-carboxylate. M.p.: 157° to 160° C.

Example 227

Octyl 2-methyl-5-oxo-4-(2-trifluoromethylphenyl)-1,4,5,7-tetrahydrofuro[3,4-b]pyridine-3-carboxylate. M.p.: 119° to 120° C.

Example 228

Ethyl 4-(2,3-dichlorophenyl)-2-methyl-5-oxo-1,4,5,7-tetrahydrofuro[3,4-b]pyridine-3-carboxylate. M.p.: 249° to 251° C.

Example 229

Ethyl 2-methyl-5-oxo-4-(3-pyridyl)-1,4,5,7-tetrahydrofuro[3,4-b]pyridine-3-carboxylate. M.p.: 192° to 194° C.

Example 230

Ethyl 2-methyl-5-oxo-4-(2-trifluoromethoxyphenyl)-1,4,5,7-tetrahydrofuro[3,4-b]pyridine-3-carboxylate. M.p.: 174° to 176° C.

Example 231

Ethyl 2-methyl-4-(2-naphthyl)-5-oxo-1,4,5,7-tetrahydrofuro[3,4-b]pyridine-3-carboxylate. M.p.: >270° C.

Example 232

Ethyl 5-oxo-4-(2-trifluoromethylphenyl)-1,2,7-trimethyl-1,4,5,7-tetrahydrofuro[3,4-b]pyridine-3-carboxylate. M.p.: 171° to 172° C.

Example 233

Ethyl 2-methyl-5-oxo-4-(3-trifluoromethylphenyl)-1,4,5,7-tetrahydrofuro[3,4-b]pyridine-3-carboxylate. M.p.: 180° to 182° C.

Example 234

Ethyl 2-ethyl-5-oxo-4-(2-trifluoromethylphenyl)-1,4,5,7-tetrahydrofuro[3,4-b]pyridine-3-carboxylate. M.p.: 237° to 239° C.

Example 235

Allyl 2-methyl-5-oxo-4-(2-trifluoromethylphenyl)-1,4,5,7-tetrahydrofuro[3,4-b]pyridine-3-carboxylate. M.p.: 190° to 192° C.

Example 236

Ethyl 1,2-dimethyl-5-oxo-4-(2-trifluoromethylphenyl)-1,4,5,7-tetrahydrofuro[3,4-b]pyridine-3-carboxylate. M.p.: 196° to 197° C.

Example 237

Methyl 4-[(2-fluoro-3-chloro)phenyl]-2-methyl-5-oxo-1,4,5,7-tetrahydrofuro[3,4-b]pyridine-3-carboxylate. M.p.: 220° to 223° C.

Example 238

Butyl 4-[2-(cyclohexylmethylthio)-phenyl]-2-methyl-5-oxo-1,4,5,7-tetrahydrofuro[3,4-b]pyridine-3-carboxylate.
M.p.: 123° to 128° C.

Example 239

Ethyl 4-[2-(cyclohexylmethylthio)-phenyl]-2-methyl-5-oxo-1,4,5,7-tetrahydrofuro[3,4-b]pyridine-3-carboxylate.
M.p.: 77° to 82° C.

Example 240

Hexyl 2-methyl-5-oxo-4-(2-trifluoromethylphenyl)-1,4,5,7-tetrahydrofuro[3,4-b]pyridine-3-carboxylate. M.p.: 164° to 165° C.

Example 241

Ethyl 2-methyl-5-oxo-4-(2-phenylthiophenyl)-1,4,5,7-tetrahydrofuro[3,4-b]pyridine-3-carboxylate. M.p.: 191° to 192° C.

Example 242

Allyl 4-(2-chlorophenyl)-2-methyl-5-oxo-1,4,5,7-tetrahydrofuro[3,4-b]pyridine-3-carboxylate. M.p.: 206° C.

Analogously to the process according to Example 35, the following compounds were obtained from the corresponding diesters by hydrogenation with lithium aluminum hydride:

Example 243

Ethyl 1,4-dihydro-2,3,6-trimethyl-4-(2-chlorophenyl)-pyridine-5-carboxylate of melting point 112° C.

Example 244

Methyl 1,4-dihydro-2,3,6-trimethyl-4-(4-chlorophenyl)-pyridine-5-carboxylate of melting point 94° C.

Example 245

Methyl 1,4-dihydro-2,3,6-trimethyl-4-(2-methylphenyl)-pyridine-5-carboxylate of melting point 147° to 153° C.

Example 246

Methyl 1,4-dihydro-2,3,6-trimethyl-4-[2-(4-methylbenzylthio)-phenyl]-pyridine-5-carboxylate of melting point 109° to 111° C.

Example 247

Methyl 1,4-dihydro-2,3,6-trimethyl-4-(2-trifluoromethylphenyl)-pyridine-5-carboxylate of melting point 145° to 149° C.

Example 248

Methyl 1,4-dihydro-2,3,6-trimethyl-4-(4-methylphenyl)-pyridine-5-carboxylate of melting point 146° to 150° C.

Example 249

Methyl 1,4-dihydro-2,3,6-trimethyl-4-(3-thienyl)-pyridine-5-carboxylate of melting point 150° to 158° C.

Example 250

Methyl 1,4-dihydro-2,3,6-trimethyl-4-(2-benzyloxyphenyl)-pyridine-5-carboxylate, isolated as a colorless resin. Mass spectrum: The most important peaks are found at: m/e=363, 348, 304, 272, 180.

Example 251

Methyl 1,4-dihydro-2,3,6-trimethyl-4-[2-(4-chlorobenzyloxy)-phenyl]-pyridine-5-carboxylate, isolated as a colorless resin. Mass spectrum: m/e=396 (180).

Example 252

Methyl 1,4-dihydro-2,3,6-trimethyl-4-[2-(2,6-dichlorobenzyloxy)-phenyl]-pyridine-5-carboxylate, isolated as an oil.

Example 253

Methyl 1,4-dihydro-2,3,6-trimethyl-4-[2-(4-methylbenzyloxy)-phenyl]-pyridine-5-carboxylate, isolated as an oil.

Example 254

Methyl 1,4-dihydro-2,3,6-trimethyl-4-(2-phenethyloxyphenyl)-pyridine-5-carboxylate, isolated as a yellow oil.

Example 255

Methyl 1,4-dihydro-2,3,6-trimethyl-4-(2-phenylmercaptomethoxyphenyl)-pyridine-5-carboxylate, isolated as a yellow oil.

Mass spectrum: m/e=395 (180).

Example 256

Methyl 1,4-dihydro-2,3,6-trimethyl-4-[3-(4-methylbenzyloxy)-phenyl]-pyridine-5-carboxylate, isolated as a yellow oil.

Example 257

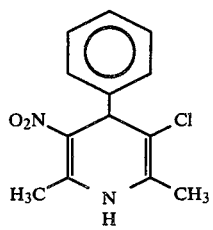

3-Chloro-1,4-dihydro-2,6-dimethyl-5-nitro-4-phenyl-pyridine of melting point 192° C. (isopropanol) was obtained analogously to Example 18, by heating 0.1 mol of 2-amino-1-nitro-prop-1-ene and 0.1 mol of 2-chloro-1-phenyl-but-1-ene-3-one in boiling ethanol. Yield: 28% of theory.

Example 258

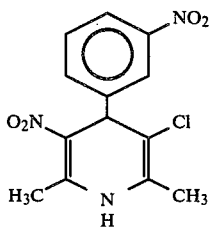

0.1 mol of 2-amino-1-nitro-prop-1-ene and 0.1 mol of 2-chloro-1-(3-nitrophenyl)-but-1-ene-3-one were heated in boiling ethanol, analogously to Example 18. 3-Chloro-1,4-dihydro-2,6-dimethyl-5-nitro-4-(3-nitrophenyl)pyridine of melting point 198° C. (decomposition) was obtained. Yield:

Example 259

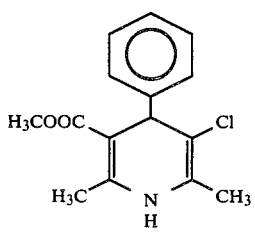

0.1 mol of methyl aminocrotonate and 2-chloro-1-phenyl-but-1-ene-3-one were heated in boiling ethanol, analogously to Example 18. Methyl-3-chloro-1,4-dihydro-2,6-dimethyl-4-phenyl-pyridine-5-carboxylate of melting point 147° C. was obtained. Yield: 23% of theory.

Example 260

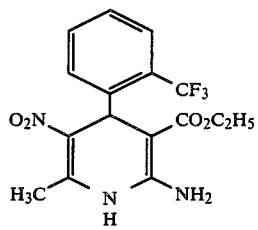

2-Amino-1,4-dihydro-6-methyl-5-nitro-4-(2-trifluoromethylphenyl)-pyridine-5-carboxylic acid ethyl ester of melting point 210° C. (isopropanol) was obtained analogously to Example 18, by the reaction of 2-nitro-1-(2-trifluoromethylphenyl)-but-1-ene-3-one and ethyl amidinoacetate in ethanol.

Yield 32% of theory.

Example 261

Methyl 4-(2-benzylthiophenyl)-3-cyano-1,4-dihydro-2,6-dimethyl-pyridine-5-carboxylate

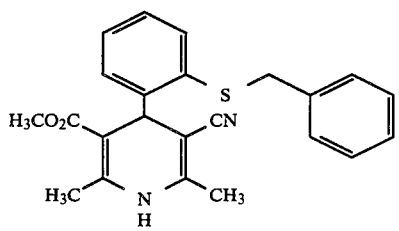

A solution of 22.7 g (69 millimols) of methyl 2-(2-benzylthiobenzylidene)-acetoacetate and 5.7 g (69 millimols) of β-aminocrotonic acid nitrile in 80 ml of methanol was heated at the boil for 12 hours under nitrogen. The solvent was then concentrated down in vacuo, and the oily residue was crystallized by trituration with a small amount of ether. The crude product was filtered off under suction and recrystallized from methanol.

Melting point: 183°–185° C.

Yield: 15.7 g (58%)

Example 262

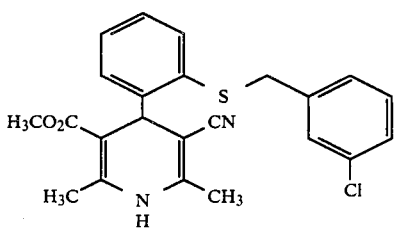

Methyl 4-(2-(3-chlorobenzylthio)-phenyl)-3-cyano-1,4-dihydro-2,6-dimethylpyridine-5-carboxylate of m.p.: 155° C. (methanol) was obtained analogously to Example 261, by the reaction of methyl 2-(2-(3-chlorobenzylthio)benzylidene)-acetoacetate and β-aminocrotonic acid nitrile in methanol.

Yield: 51% of theory.

Example 263

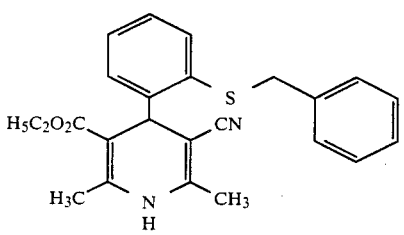

Ethyl 4-(2-benzylthiophenyl)-3-cyano-1,4-dihydro-2,6-dimethyl-pyridine-5-carboxylate of m.p.: 127° C. was obtained analogously to Example 261, by the reaction of ethyl 2-(2-benzylthiobenzylidene)-acetoacetate and β-aminocrotonic acid nitrile in ethanol. Yield: 49% of theory.

Example 264

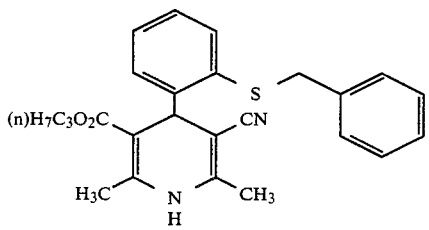

n-Propyl 4-(2-benzylthiophenyl)-3-cyano-1,4-dihydro-2,6-dimethyl-pyridine-5-carboxylate of m.p.: 101° C. was obtained analogously to Example 261, by the reaction of n-propyl 2-(2-benzylthiobenzylidene)-acetoacetate and β-aminocrotonic acid nitrile in ethanol. Yield: 45% of theory.

Example 265

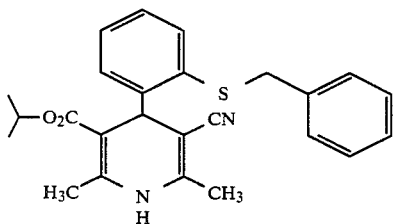

Isopropyl 4-(2-benzylthiophenyl)-3-cyano-1,4-dihydro-2,6-dimethylpyridine-5-carboxylate of m.p.: 152° C. was obtained analogously to Example 261, by the reaction of isopropyl 2-(2-benzylthiobenzylidene)-acetoacetate and β-aminocrotonic acid nitrile in ethanol.

Yield: 61% of theory.

It is understood that the specification and examples are illustrative but not limitative of the present invention and that other embodiments within the spirit and scope of the invention will suggest themselves to those skilled in the art.

What is claimed is:

1. A method for augmenting contractility of the heart or for the treatment of hypotonic circulatory conditions, for the depression of the blood sugar, for decreasing the swelling of mucous membranes or for influencing the salt and fluid balance, in human and non-human animals, which comprises administering to the animals an effective amoung of a 1,4-dihydropyridine which exhibits positive inotropic activity and is of the formula

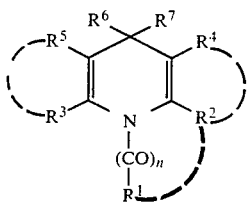

in the form of an individual isomer, an isomer mixture, a racemate or an optical antipode, or a pharmaceutically acceptable salt thereof, in which n is 0, 1 or 2, $R^1$ (a) represents a hydrogen atom, a straight-chain, branched, cyclic, saturated or unsaturated aliphatic hydrocarbon radical which has up to 10 carbon atoms and optionally contains 1 or 2 identical or different hetero chain members selected from O, CO, S, $SO_2$, =N— or $NR^I$, this hydrocarbon radical being optionally substituted by halogen, $NO_2$, CN, $N_3$, hydroxyl, phenyl, naphthyl or heteroaryl, or (b) represents a phenyl, naphthyl or heteroaryl radical, these radicals optionally carrying 1 to 3 identical or different substituents selected from phenyl; alkyl, alkenyl, alkinyl, alkenoxy, and alkinoxy, each having up to 4 carbon atoms; aralkyl having 7 to 14 carbon atoms; acyl having up to 6 carbon atoms; alkylene; dioxyalkylene having up to 4 carbon atoms in the alkylene chain; halogen; $CF_3$; $OCF_3$, $SCF_3$; $NO_2$; CN; $N_3$; $COR^{IV}$; $COOR^V$; $OR^{VI}$; $NR^I$ and $NR^{VII}R^{VIII}$; and it being possible for the alkyl, alkoxy and aryl radicals of the above-mentioned substituents to be substituted in turn by halogen, $COOR^V$ or $NR^{VII}R^{VIII}$, or (c) represents a radical of the formula $NR^{VII}R^I$, (the radicals $R^I$, $R^{II}$, $R^{IV}$, $R^V$, $R^{VI}$, $R^{VII}$ and $R^{VIII}$ mentioned under (a), (b) and (c), immediately above having the meanings given below), $R^2$ (a), independently of $R^1$, has any of these meanings given immediately above for $R^1$, or (b) represents a radical of the formula $NHR^I$ or

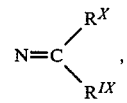

($R^I$, $R^{IX}$ and $R^X$ having the meanings give below), or $R^1$ and $R^2$ together form a 5-membered to 7-membered saturated or unsaturated ring which optionally contains one or two identical or different ring members selected from O, S, $NR^I$ and CO, and which optionally contains one to three identical or different substituents selected from halogen; hydroxyl; alkyl and alkoxy, each having 1 to 4 carbon atoms; phenyl; naphthyl; and aralkyl having 7 to 14 carbon atoms, $R^3$, independently of $R^2$ has any of those meanings given immediately above for $R^2$, with the proviso that only one of the substituents $R^2$ or $R^3$ can represent alkoxy, alkylthio or $NHR^I$ in each instance, $R^4$ and $R^5$ are identical or different and each (a) represents a hydrogen atom, $NO_2$, $NO$, $CN$, $SO_m-R^{IX}$ (in which m is 0 or 2), a halogen atom,

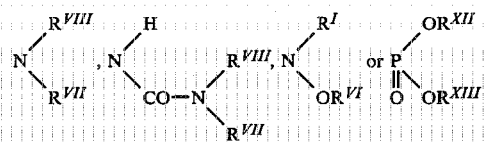

(wherein $R^I$, $R^{VI}$, $R^{VII}$, $R^{VIII}$, $R^{IX}$ $R^{XII}$ and $R^{XIII}$ have the meanings given below), or (b) represents a branched or unbranched cyclic, saturated or unsaturated aliphatic hydrocarbon radical which has up to 10 carbon atoms and is optionally substituted by halogen, OH, CN, alkoxy and alkylthio, each having 1 to 4 carbon atoms, phenyloxy, naphthoxy, $COOR^V$ or

(wherein $R^V$, $R^{VII}$ and $R^{VIII}$ have the meanings given below), or (c) represents an aromatic hydrocarbon radical having 6 to 10 carbon atoms, or a 5-membered to 7-membered saturated or unsaturated hetero ring having 1 to 3 identical or different hetero members selected from O, S, —N=, $NR^I$ ($R^I$ having the meaning given below), and this hetero ring is linked to the dihydropyridine ring either via a carbon atom or a nitrogen atom, and the aromatic hydrocarbon radical and hetero rings optionally carry 1 to 3 identical or different substituents selected from halogen; OH; CN; $CF_3$; $OCF_3$, $SCF_3$; $NO_2$; alkyl and alkoxy, each having 1 to 4 carbon atoms; phenyl; naphthyl; and

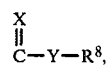

($R^{VII}$ and $R^{VIII}$ having the meanings given below), (d) represents a radical of the general formula $$\overset{X}{\underset{\|}{C}}-Y-R^8,$$

wherein X denotes oxygen, sulphur or $NR^I$, and Y represents a single bond, O, S or $NR^I$ ($R^I$ having the meaning given below), and $R^8$ independently of $R^1$, has any of those meanings given immediately above for $R^1$, or (e) represents a radical of the formula.

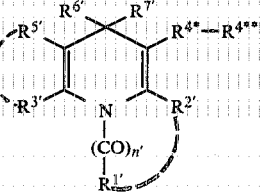

wherein n', $R^{1'}$, $R^{2'}$, $R^{3'}$, $R^{5'}$, $R^{6'}$ and $R^{7'}$, independently of n, $R^1$, $R^2$, $R^3$, $R^5$, $R^6$, and $R^7$, have any of those meanings respectively given immediately above for n, $R^1$, $R^2$, $R^3$, $R^5$, $R^6$, and $R^7$, and $R^{4*}$ and $R^{4**}$ are identical or different and each represents a radical, minus a hydrogen, of the substituents given immediately above for $R^4$ under (a) to (d), or each pair of, $R^2$ and $R^4$, and/or $R^3$ and $R^5$, independently together form a branched, straight-chain, saturated or unsaturated 5-membered to 7-membered ring which optionally contains 1, 2 or 3 identical or different ring members selected from O, CO, CS, $C=NR^I$, =N—, $NR^I$ and $SO_m$ (in which m is 0 or 2), and which is optionally substituted by halogen, hydroxyl, alkoxy having 1 to 4 carbon atoms, phenyl, naphthyl, aralkyl having 7 to 14 carbon atoms,

or is disubstituted by a straight-chain or branched alkylene chain having 3 to 8 carbon atoms, it also being possible for this common ring of $R^2$ and $R^4$ to be directly fused with the common ring of $R^1$ and $R^2$, (the radicals $R^I$, $R^{II}$, $R^{III}$, $R^{VII}$ and $R^{VIII}$ having the meanings give below), $R^6$ represents a hydrogen atom or an alkyl or halogenoalkyl radical each having 1 to 4 carbon atoms, and $R^7$ (a) represents a saturated, unsaturated cyclic, straight-chain or branched aliphatic hydrocarbon radical which has up to 10 carbon atoms and is optionally substituted by halogen, phenyl, naphthyl or heteroaryl, or (b) represents a phenyl, naphthyl or heteroaryl radical which optionally contains 1 to 3 identical or different substituents selected from $NO_2$; halogen; CN; $N_3$; NO; $CF_3$;

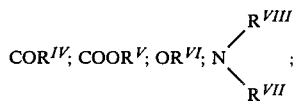

alkyl having 1 to 4 carbon atoms, phenyl; naphthyl; alkenyl, alkinyl, alkenoxy, and alkinoxy, each having up to 4 carbon atoms; aralkyl having 7 to 14 carbon atoms; acyl having 1 to 4 carbon atoms; alkylene or dioxyalkylene, each having up to 4 carbon atoms; and the above-mentioned alkyl and aryl substituents in turn can be substituted by halogen, COOR$^V$ or

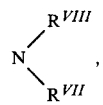

and, in the above-mentioned definitions of the substituents $R^1$ to $R^7$, $R^I$ represents a hydrogen atom, an alkyl radical having 1 to 6 carbon atoms, a phenyl or naphthyl radical, an aralkyl radical having 7 to 12 carbon atoms, a heteroaryl radical or an acyl radical having up to 7 carbon atoms, $R^{II}$ and $R^{III}$ are identical or different and each represents an alkyl radical having 1 to 6 carbon atoms, a phenyl radical, a naphthyl radical, an aralkyl radical having 7 to 12 carbon atoms or a heteroaryl radical, $R^{IV}$, $R^V$ and $R^{VI}$ are each identical or different and represent a hydrogen atom, an alkyl radical having 1 to 6 carbon atoms, a phenyl or naphthyl radical, an aralkyl radical having 7 to 12 carbon atoms or a heteroaryl radical, $R^{VII}$ and $R^{VIII}$ are each identical or different and represent a hydrogen atom, a phenyl or naphthyl radical an aralkyl radical having 7 to 12 carbon atoms, or an alkyl radical which has 1 to 6 carbon atoms and which is optionally interrupted by O, S or $NR^I$, or $R^{VII}$ and $R^{VIII}$, together with the nitrogen atom, form a 5-membered to 7-membered ring which can contain 1 or 2 identical or different hetero ring members selected from O, S or $NR^I$, or one of the radicals $R^{VII}$ and $R^{VIII}$ represents an aliphatic acyl group having up to 6 carbon atoms, $R^{IX}$, $R^X$, $R^{XI}$, $R^{XII}$, and $R^{XIII}$ are each identical or different and represent an alkyl radical having 1 to 6 carbon atoms, a phenyl or naphthyl radical or an aralkyl radical having 7 to 12 carbon atoms.

2. The method according to claim 1 wherein the 1,4-dihydro pyridine is

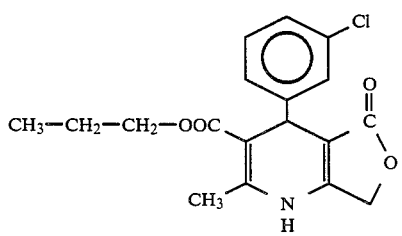

3. The method according to claim 1 wherein the 1,4-dihydropyridine is

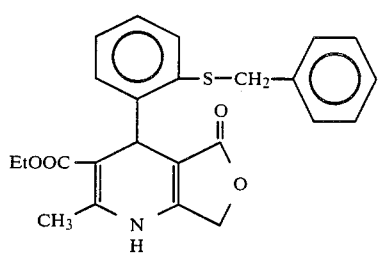

4. The method according to claim 1 wherein the 1,4-dihydropyridine is

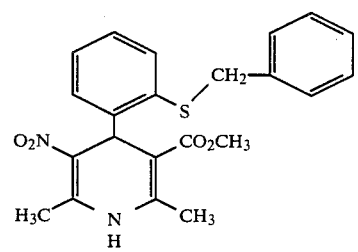

5. The method according to claim 1 wherein the 1,4-dihydropyridine is

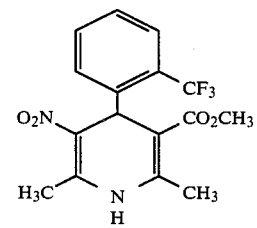

6. The method according to claim 1 wherein the 1,4-dihydropyridine is .

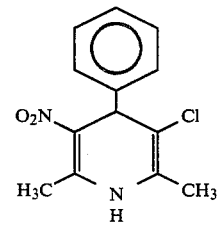

7. The method according to claim 1 wherein the 1,4-dihydropyridine is

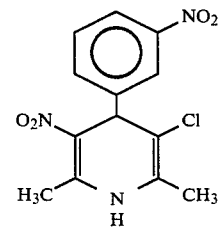

8. The method according to claim 1 wherein the 1,4-dihydropyridine is

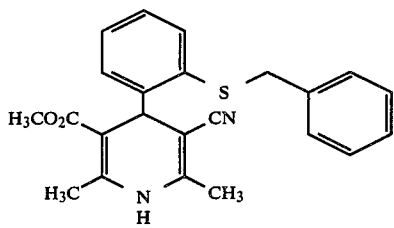

9. The method according to claim 1, wherein the dihydropyridine is administered for augmenting contractility of the heart.

10. The method according to claim 1, wherein the dihydropyridine is administered for the treatment of a hypotonic circulatory condition.

11. The method according to claim 1, wherein dihydropyridine is administered for depressing blood sugar.

12. The method according to claim 1, wherein dihydropyridine is administered for decreasing the swelling of mucous membranes.

13. The method according to claim 1, wherein the dihydropyridine is administered for influencing the salt and fluid balance.

* * * * *